United States Patent
Nalagatla et al.

(10) Patent No.: US 11,141,777 B2
(45) Date of Patent: Oct. 12, 2021

(54) MULTI-PIECE JAW ASSEMBLY FOR SURGICAL CLIP APPLIER

(71) Applicant: ETHICON LLC, Guaynabo, PR (US)

(72) Inventors: Anil K. Nalagatla, Mason, OH (US); Frederick E. Shelton, IV, Hillsboro, OH (US); Chester O. Baxter, III, Loveland, OH (US); Amit Gupta, Pune (IN); Mayukh Bhattacharya, Kolkata (IN)

(73) Assignee: Cilag GmbH International, Zug (CH)

( * ) Notice: Subject to any disclaimer, the term of this patent is extended or adjusted under 35 U.S.C. 154(b) by 145 days.

(21) Appl. No.: 16/236,682

(22) Filed: Dec. 31, 2018

(65) Prior Publication Data

US 2020/0206805 A1    Jul. 2, 2020

(51) Int. Cl.
| | |
|---|---|
| *B21K 5/00* | (2006.01) |
| *A61B 17/128* | (2006.01) |
| *B23K 26/38* | (2014.01) |
| *A61B 17/00* | (2006.01) |

(52) U.S. Cl.
CPC .......... *B21K 5/00* (2013.01); *A61B 17/1285* (2013.01); *B23K 26/38* (2013.01); *A61B 2017/00526* (2013.01)

(58) Field of Classification Search
CPC .... A61B 17/1285; A61B 17/128; B22F 3/225
See application file for complete search history.

(56) References Cited

U.S. PATENT DOCUMENTS

| | | |
|---|---|---|
| 3,777,538 A | 12/1973 | Weatherly et al. |
| 5,163,945 A | 11/1992 | Ortiz et al. |
| 5,205,459 A | 4/1993 | Brinkerhoff et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,292,053 A | 3/1994 | Bilotti et al. |

(Continued)

FOREIGN PATENT DOCUMENTS

| | | |
|---|---|---|
| DE | 20 2009 006113 U1 | 7/2009 |
| EP | 0 086 721 A2 | 8/1983 |

(Continued)

OTHER PUBLICATIONS

European Search Report, Partial, and Provisional Written Opinion dated Mar. 24, 2020 for Application No. EP 19220098.8, 16 pgs.

(Continued)

*Primary Examiner* — Jacob J Cigna
(74) *Attorney, Agent, or Firm* — Frost Brown Todd LLC

(57) ABSTRACT

A method is used to manufacture a surgical instrument configured to apply a surgical clip to a patient. The surgical instrument includes a jaw retaining assembly. The jaw retaining assembly includes a shaft and opposing first and second jaws. The method includes metal injection molding a first metallic portion of the jaw retaining assembly. The method also includes metal injection molding, stamping, and/or laser cutting a second metallic portion of the jaw retaining assembly, wherein the second metallic portion is separately formed from the first metallic portion. The method also includes fixably coupling the first and second metallic portions of the jaw retaining assembly together.

18 Claims, 22 Drawing Sheets

(56) References Cited

U.S. PATENT DOCUMENTS

| | | | | |
|---|---|---|---|---|
| 5,333,773 | A | 8/1994 | Main et al. | |
| 5,342,373 | A | 8/1994 | Stefanchik et al. | |
| 5,350,104 | A | 9/1994 | Main et al. | |
| 5,383,881 | A * | 1/1995 | Green | A61B 17/128 606/142 |
| 5,403,312 | A | 4/1995 | Yates et al. | |
| 5,423,835 | A * | 6/1995 | Green | A61B 17/1285 227/901 |
| 5,431,668 | A | 7/1995 | Burbank, III et al. | |
| 5,445,167 | A | 8/1995 | Yoon et al. | |
| 5,533,661 | A | 7/1996 | Main et al. | |
| 5,601,573 | A | 2/1997 | Fogelberg et al. | |
| 5,607,436 | A | 3/1997 | Pratt et al. | |
| 5,779,718 | A | 7/1998 | Green et al. | |
| 5,925,064 | A * | 7/1999 | Meyers | A61B 17/062 606/205 |
| 5,951,574 | A | 9/1999 | Stefanchik et al. | |
| 6,159,200 | A | 12/2000 | Verdura et al. | |
| 6,824,547 | B2 | 11/2004 | Wilson et al. | |
| 6,988,650 | B2 | 1/2006 | Schwemberger et al. | |
| 7,000,818 | B2 | 2/2006 | Shelton, IV et al. | |
| 7,134,587 | B2 | 11/2006 | Schwemberger et al. | |
| 7,147,140 | B2 | 12/2006 | Wukusick et al. | |
| 7,204,404 | B2 | 4/2007 | Nguyen et al. | |
| 7,207,472 | B2 | 4/2007 | Wukusick et al. | |
| 7,261,724 | B2 | 8/2007 | Molitor et al. | |
| 7,380,696 | B2 | 6/2008 | Shelton, IV et al. | |
| 7,422,139 | B2 | 9/2008 | Shelton, IV et al. | |
| 7,464,849 | B2 | 12/2008 | Shelton, IV et al. | |
| 7,670,334 | B2 | 3/2010 | Hueil et al. | |
| 7,686,820 | B2 | 3/2010 | Huitema et al. | |
| 7,699,860 | B2 | 4/2010 | Huitema et al. | |
| 7,731,724 | B2 | 6/2010 | Huitema et al. | |
| 7,753,245 | B2 | 7/2010 | Boudreaux et al. | |
| 7,842,045 | B2 * | 11/2010 | Vandenbroek | A61B 17/128 606/142 |
| 7,845,537 | B2 | 12/2010 | Shelton, IV et al. | |
| 7,980,443 | B2 | 7/2011 | Scheib et al. | |
| 8,038,686 | B2 | 10/2011 | Huitema et al. | |
| 8,210,411 | B2 | 7/2012 | Yates et al. | |
| 8,220,688 | B2 | 7/2012 | Laurent et al. | |
| 8,262,679 | B2 | 9/2012 | Nguyen | |
| 8,308,040 | B2 | 11/2012 | Huang et al. | |
| 8,393,514 | B2 | 3/2013 | Shelton, IV et al. | |
| 8,408,439 | B2 | 4/2013 | Huang et al. | |
| 8,453,914 | B2 | 6/2013 | Laurent et al. | |
| 8,561,870 | B2 | 10/2013 | Baxter, III et al. | |
| 8,608,045 | B2 | 12/2013 | Smith et al. | |
| 8,733,613 | B2 | 5/2014 | Huitema et al. | |
| 8,910,847 | B2 | 12/2014 | Nalagatla et al. | |
| 9,072,535 | B2 | 7/2015 | Shelton, IV et al. | |
| 9,101,358 | B2 | 8/2015 | Kerr et al. | |
| 9,186,142 | B2 | 11/2015 | Fanelli et al. | |
| 9,345,481 | B2 | 5/2016 | Hall et al. | |
| 9,439,670 | B2 * | 9/2016 | Witt | A61B 17/320092 |
| 9,517,065 | B2 | 12/2016 | Simms et al. | |
| 9,713,469 | B2 | 7/2017 | Leimbach et al. | |
| 9,717,497 | B2 | 8/2017 | Zerkle et al. | |
| 9,795,379 | B2 | 10/2017 | Leimbach et al. | |
| 9,808,248 | B2 | 11/2017 | Hoffman | |
| 9,839,421 | B2 | 12/2017 | Zerkle et al. | |
| 9,867,615 | B2 | 1/2018 | Fanelli et al. | |
| 9,907,552 | B2 | 3/2018 | Measamer et al. | |
| 9,924,945 | B2 | 3/2018 | Zheng et al. | |
| 9,931,123 | B2 | 4/2018 | Blake, III | |
| 9,936,949 | B2 | 4/2018 | Measamer et al. | |
| 10,092,292 | B2 | 10/2018 | Boudreaux et al. | |
| 2001/0025184 | A1 * | 9/2001 | Messerly | A61B 17/320092 606/169 |
| 2005/0139636 | A1 | 6/2005 | Schwemberger et al. | |
| 2005/0143759 | A1 | 6/2005 | Kelly | |
| 2005/0145672 | A1 | 7/2005 | Schwemberger et al. | |
| 2006/0074417 | A1 * | 4/2006 | Cunningham | A61B 18/1442 606/51 |
| 2006/0161182 | A1 * | 7/2006 | Vandenbroek | A61B 17/128 606/142 |
| 2007/0175955 | A1 | 8/2007 | Shelton, IV et al. | |
| 2007/0213712 | A1 * | 9/2007 | Buysse | A61B 18/1442 606/51 |
| 2014/0239037 | A1 | 8/2014 | Boudreaux et al. | |
| 2014/0263552 | A1 | 9/2014 | Hall et al. | |
| 2015/0083772 | A1 | 3/2015 | Miller et al. | |
| 2015/0083773 | A1 | 3/2015 | Measamer et al. | |
| 2015/0083774 | A1 | 3/2015 | Measamer et al. | |
| 2015/0083775 | A1 | 3/2015 | Leimbach et al. | |
| 2016/0374672 | A1 | 12/2016 | Bear et al. | |
| 2017/0027571 | A1 | 2/2017 | Nalagatla et al. | |
| 2017/0056019 | A1 * | 3/2017 | Scholten | A61B 17/1285 |
| 2017/0258471 | A1 | 9/2017 | DiNardo et al. | |
| 2018/0042637 | A1 * | 2/2018 | Craig | A61B 17/320068 |
| 2018/0132849 | A1 | 5/2018 | Miller et al. | |
| 2018/0132853 | A1 | 5/2018 | Miller et al. | |
| 2018/0140352 | A1 | 5/2018 | Netzel et al. | |
| 2018/0310938 | A1 | 11/2018 | Kluener et al. | |
| 2018/0310939 | A1 | 11/2018 | Stager et al. | |
| 2018/0368842 | A1 | 12/2018 | Shelton, IV et al. | |
| 2019/0254679 | A1 * | 8/2019 | Russell | A61B 17/1285 |

FOREIGN PATENT DOCUMENTS

| | | |
|---|---|---|
| EP | 2 158 852 A1 | 3/2010 |
| EP | 2 635 220 | 9/2013 |
| EP | 2 744 427 | 6/2014 |
| EP | 3 476 334 A1 | 5/2019 |
| WO | WO 2012/061645 A1 | 5/2012 |
| WO | WO 2013/025831 A2 | 2/2013 |

OTHER PUBLICATIONS

European Search Report and Written Opinion, dated Jul. 22, 2020 for Application No. EP 19220098.8, 22 pgs.
International Search Report and Written Opinion dated Jul. 6, 2020 for Application No. PCT/IB2019/061245, 18 pgs.

* cited by examiner

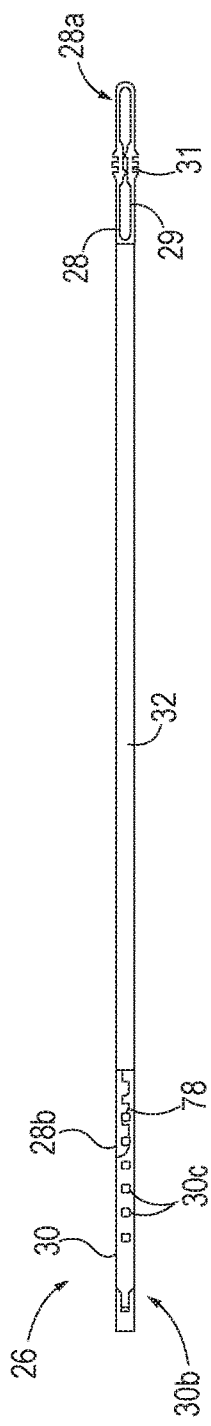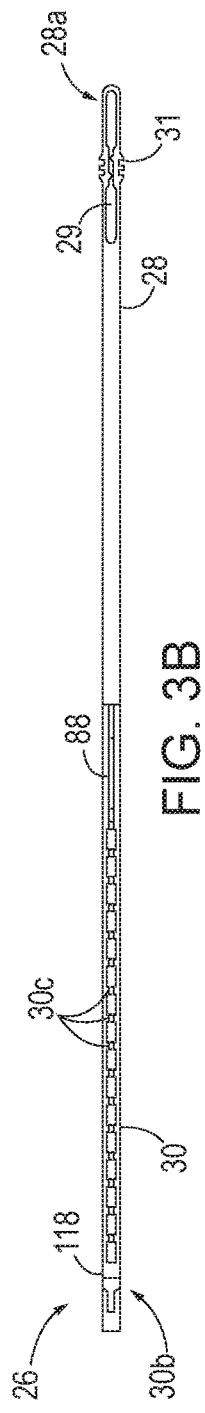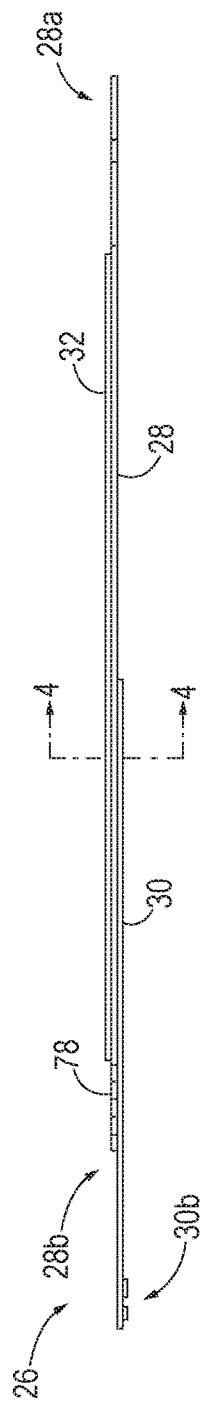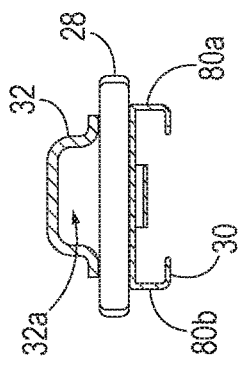

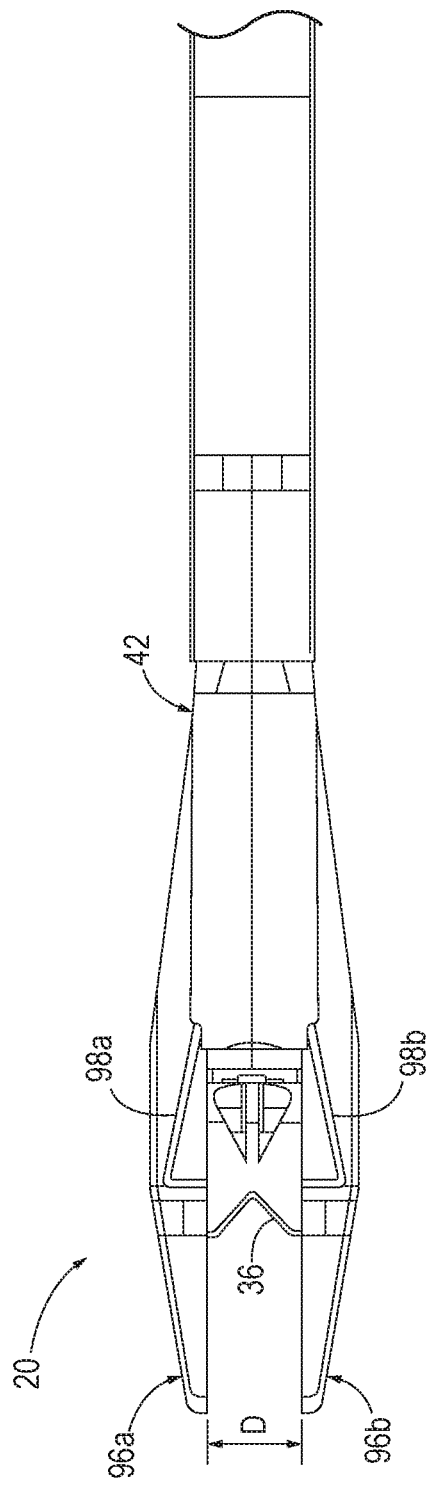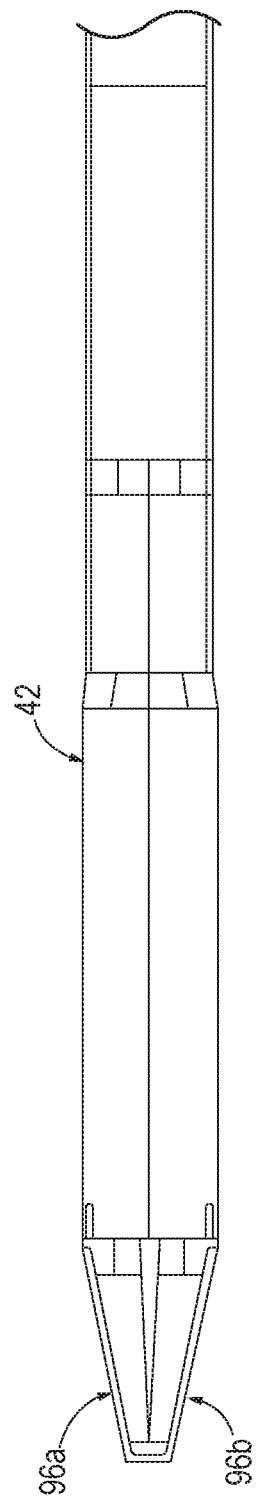
FIG. 7A
FIG. 7B

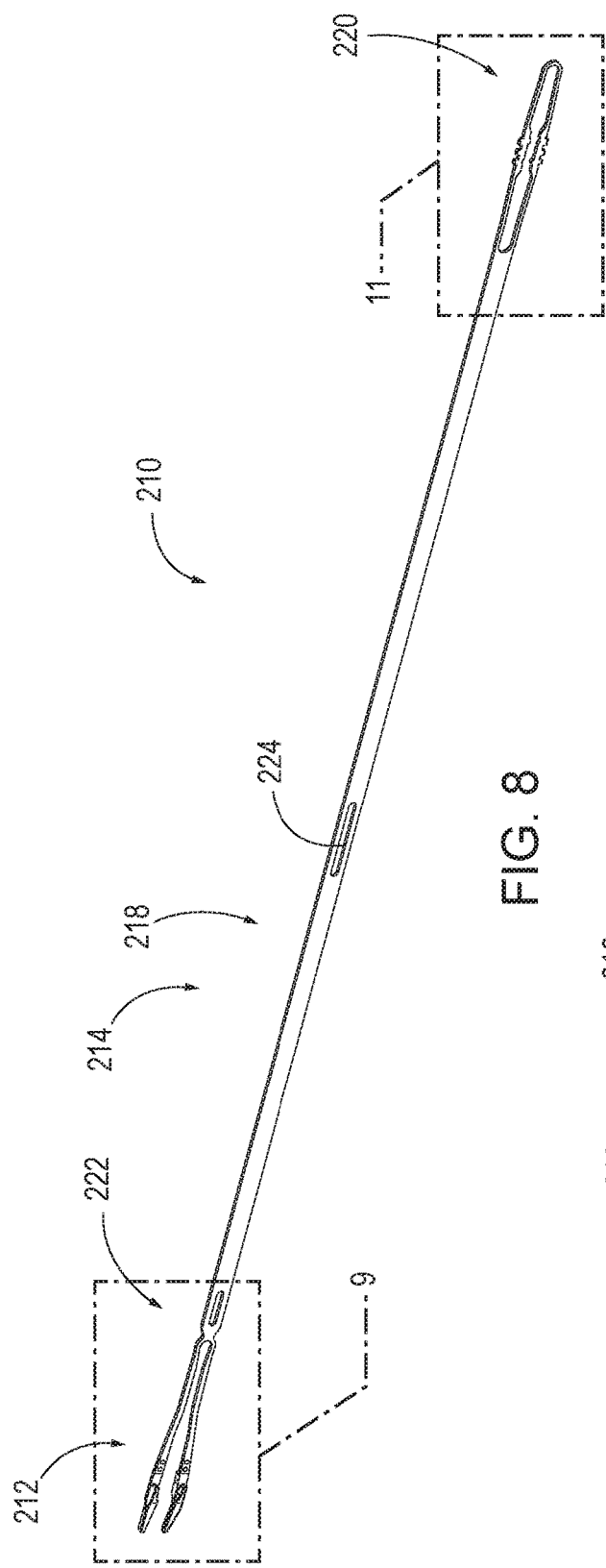
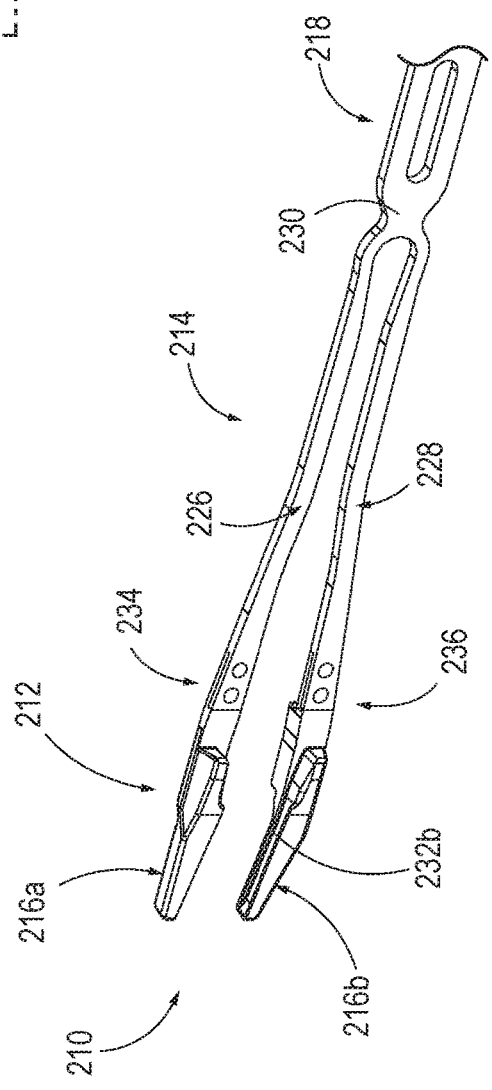
FIG. 8
FIG. 9

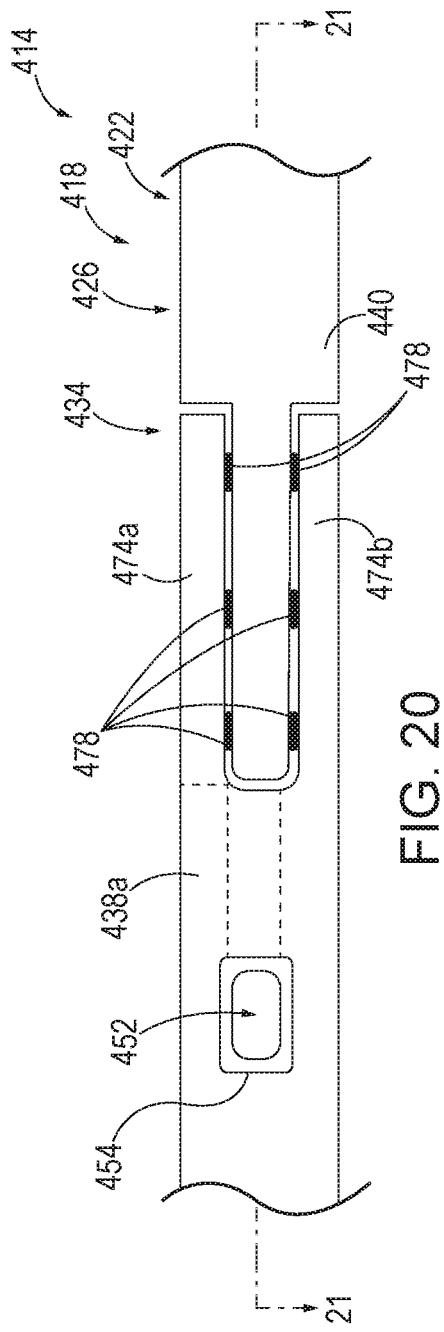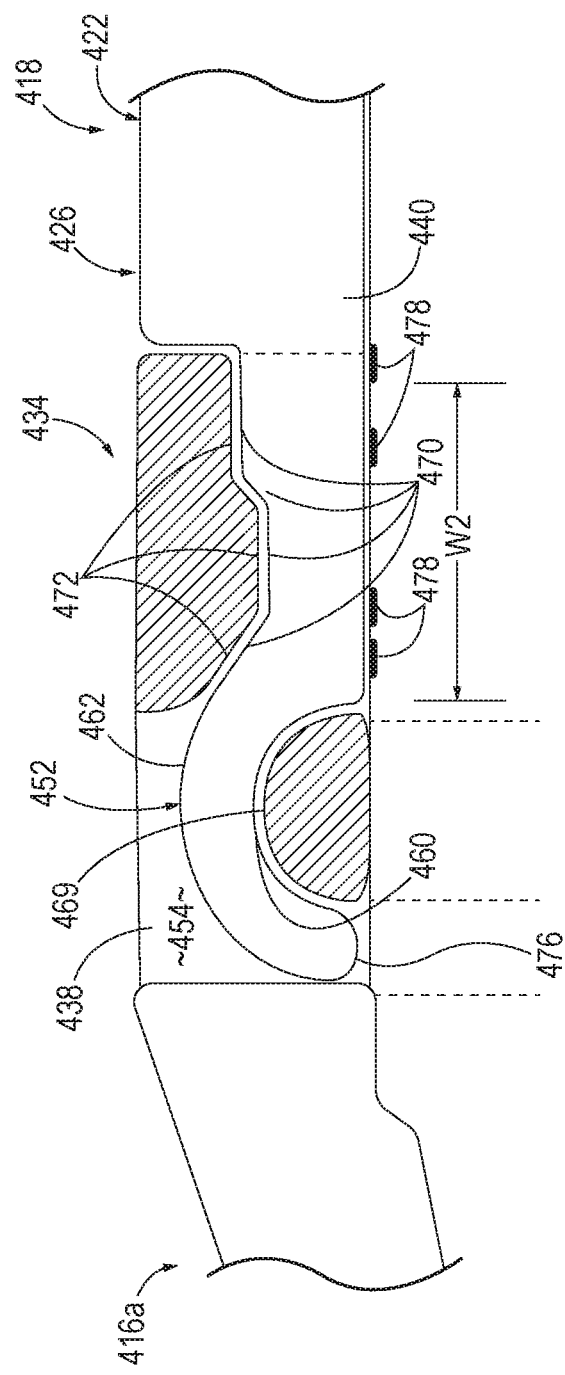

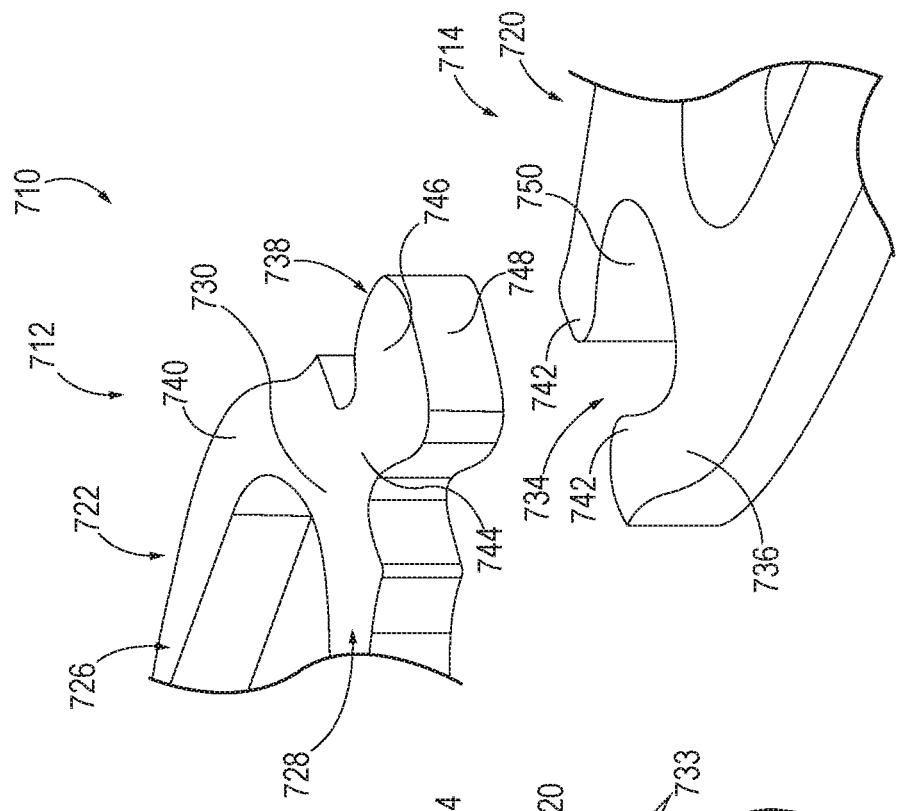
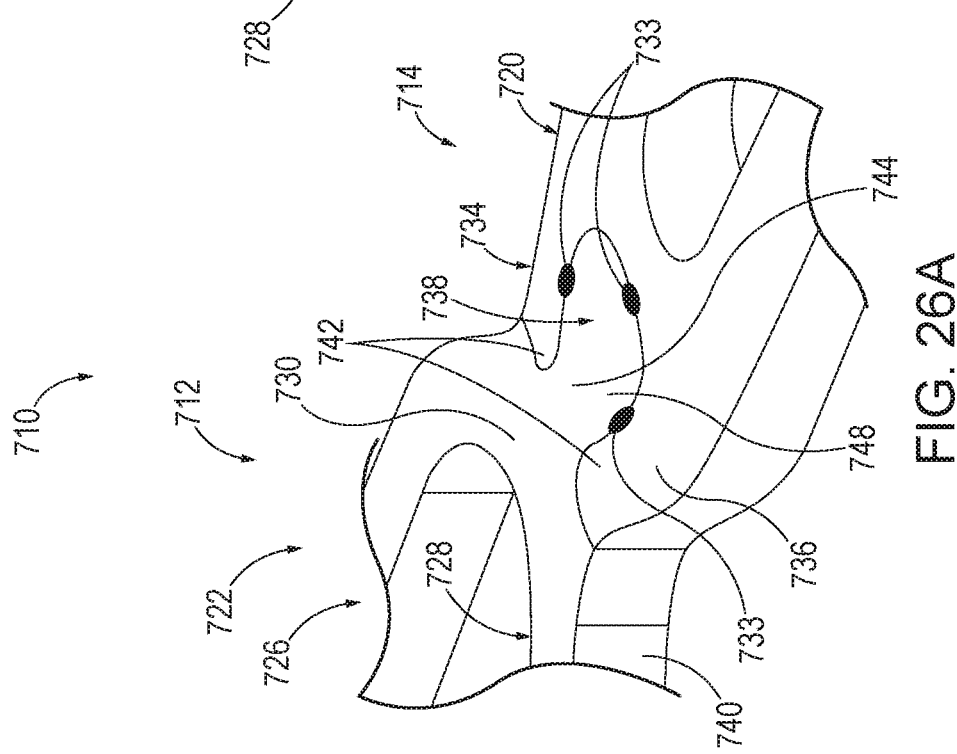
FIG. 26B
FIG. 26A

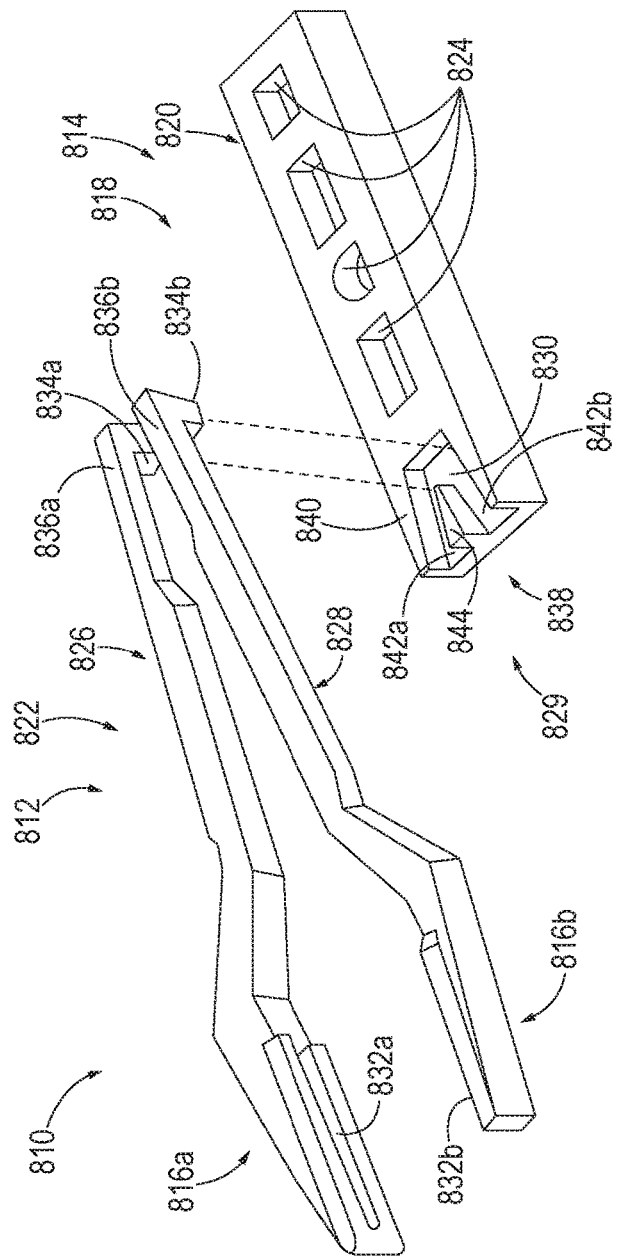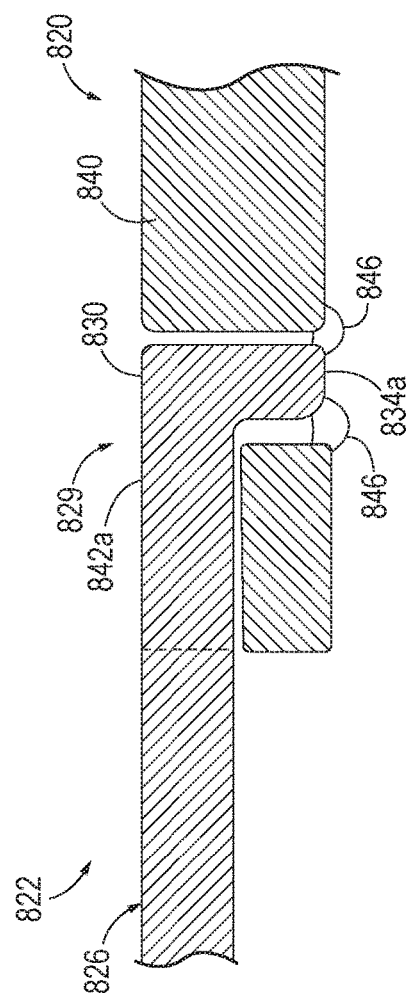
FIG. 27
FIG. 28

MULTI-PIECE JAW ASSEMBLY FOR SURGICAL CLIP APPLIER

BACKGROUND

Endoscopic surgical clip appliers may be used for a number of surgical procedures. In endoscopic or laparoscopic surgical procedures, access to the surgical site may be achieved through a trocar inserted through a small entrance incision in the skin. The trocar port allows the surgeon to insert a number of different surgical instruments therethrough and to perform surgical procedures within the patient in a minimally invasive manner.

During some surgical procedures, the surgeon may wish to terminate the flow of blood or another fluid through one or more vessels. In some such instances, the surgeon may apply a surgical clip to a blood vessel or another duct to prevent the flow of blood or other bodily fluids therethrough during the procedure. An endoscopic surgical clip applier is capable of applying a singular surgical clip or multiple surgical clips during a minimally invasive entry to the body cavity. For instance, an endoscopic surgical clip applier is capable of ligating a blood vessel by clamping a surgical clip about the blood vessel to thereby prevent blood flow through the vessel. Such clips may be fabricated from a malleable biocompatible material and may be compressed over a vessel. Alternatively, such clips may be fabricated from a resilient biocompatible material and may be released to resiliently clamp the vessel.

One example of a surgical clip applier is the LIGAMAX™ 5 by Ethicon Endo-Surgery, Inc. of Cincinnati, Ohio. Other examples of surgical clip appliers are represented by the LIGACLIP® series of surgical clip appliers by Ethicon Endo-Surgery, Inc. of Cincinnati, Ohio. Examples of surgical clips are represented by the LIGACLIP® series of surgical clips by Ethicon Endo-Surgery, Inc. of Cincinnati, Ohio. Still further examples of surgical clip appliers and surgical clips are disclosed in U.S. Pat. No. 5,163,945, entitled "Surgical Clip Applier," issued Nov. 17, 1992, the disclosure of which is incorporated by reference herein; U.S. Pat. No. 5,342,373, entitled "Sterile Clips and Instrument for their Placement," issued Aug. 30, 1994, the disclosure of which is incorporated by reference herein; U.S. Pat. No. 5,431,668, entitled "Ligating Clip Applier," issued Jul. 11, 1995, the disclosure of which is incorporated by reference herein; U.S. Pat. No. 5,445,167, entitled "Methods of Applying Surgical Clips and Suture Tie Devices to Bodily Tissue During Endoscopic Procedures," issued Aug. 29, 1995, the disclosure of which is incorporated by reference herein; U.S. Pat. No. 5,601,573, entitled "Sterile Occlusion Fasteners and Instruments and Methods for Their Placement," issued Feb. 11, 1997, the disclosure of which is incorporated by reference herein; U.S. Pat. No. 5,951,574, entitled "Multiple Clip Applier Having a Split Feeding Mechanism," issued Sep. 14, 1999, the disclosure of which is incorporated by reference herein; U.S. Pat. No. 7,261,724, entitled "Surgical Clip Advancement Mechanism," issued Aug. 28, 2007, the disclosure of which is incorporated by reference herein; U.S. Pat. No. 7,686,820, entitled "Surgical Clip Applier Ratchet Mechanism," issued Mar. 30, 2010, the disclosure of which is incorporated by reference herein; U.S. Pat. No. 7,699,860, entitled "Surgical Clip," issued Apr. 20, 2010, the disclosure of which is incorporated by reference herein; U.S. Pat. No. 7,731,724, entitled "Surgical Clip Advancement and Alignment Mechanism," issued Jun. 8, 2010, the disclosure of which is incorporated by reference herein; U.S. Pat. No. 8,038,686, entitled "Clip Applier Configured to Prevent Clip Fallout," issued Oct. 18, 2011, the disclosure of which is incorporated by reference herein; and U.S. Pat. No. 8,262,679, entitled "Clip Advancer," issued Sep. 11, 2012, the disclosure of which is incorporated by reference herein.

While various kinds of surgical clip appliers and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 3A depicts a top view of a jaw retainer assembly of the surgical clip applier of FIG. 1;

FIG. 3B depicts a bottom view of the jaw retainer assembly of FIG. 3A;

FIG. 3C depicts a side view of the jaw retainer assembly of FIG. 3B;

FIG. 4 depicts a cross-sectional view of the jaw retainer assembly of FIG. 3C taken along line 4-4 of FIG. 3C;

FIG. 7A depicts a top view of the jaws of FIG. 5 and the cam of FIG. 6 but with the cam in an initial position and the first and second opposing jaws in an open position;

FIG. 7B depicts a top view similar to FIG. 7A, but with the cam advanced over the first and second opposing jaws and the first and second opposing jaws in a closed position;

FIG. 8 depicts a perspective view of a first exemplary jaw retaining assembly including first and second opposing jaws coupled with a jaw retainer shaft;

FIG. 9 depicts an enlarged view of a distal portion of the jaw retaining assembly of FIG. 8;

FIG. 20 depicts a side view of the jaw retaining assembly of FIG. 18, with the jaw retainer shaft coupled with the first jaw;

FIG. 21 depicts a cross-sectional view of the jaw retaining assembly of FIG. 20 taken along line 21-21 of FIG. 20;

FIG. 26A depicts an enlarged portion of the jaw retaining assembly of FIG. 25 with proximal and distal portions coupled together;

FIG. 26B depicts an enlarged portion similar to FIG. 26A, but with proximal and distal portions separated from each other;

FIG. 27 depicts a front perspective view of a seventh exemplary jaw retaining assembly including first and second jaws and a shaft;

FIG. 28 depicts a sectional view of the first jaw coupled of FIG. 27 with the shaft of FIG. 27;

Figure 1:
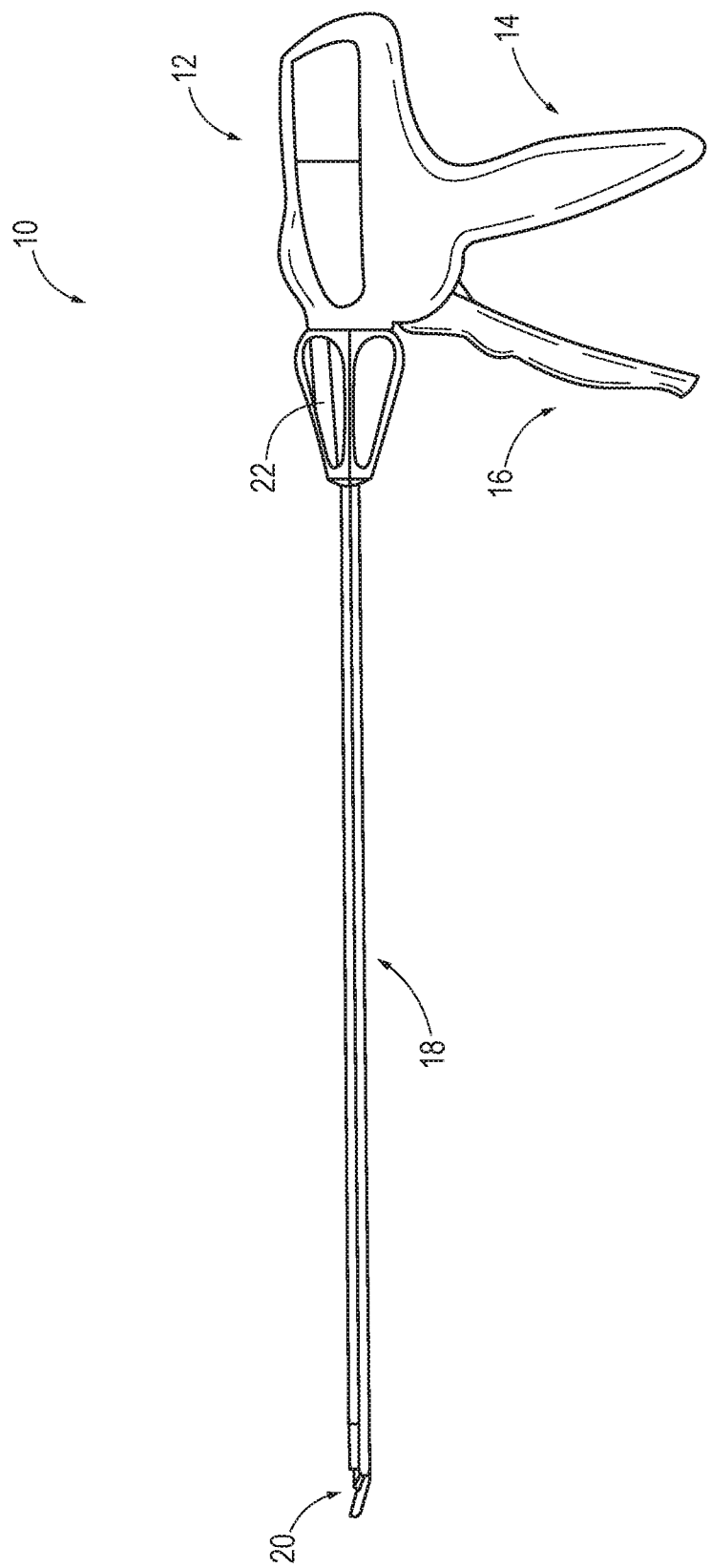
FIG. 1 depicts a side view of an exemplary surgical clip applier.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

In addition, the terms "first" and "second" are used herein to distinguish one or more portions of the surgical instrument. For example, a first assembly and a second assembly may be alternatively and respectively described as a second assembly and a first assembly. The terms "first" and "second" and other numerical designations are merely exemplary of such terminology and are not intended to unnecessarily limit the invention described herein.

I. OVERVIEW OF EXEMPLARY ENDOSCOPIC SURGICAL CLIP APPLIER

A surgical clip applier may be used to apply surgical clips to a vessel, duct, shunt, etc., during a surgical procedure. An exemplary surgical clip applier may include a variety of features to facilitate application of a surgical clip, as described herein and illustrated in the drawings. However, a person skilled in the art will appreciate that the surgical clip applier may include only some of these features and/or it may include a variety of other features known in the art. Surgical clip applier (10) described herein is merely intended to represent certain exemplary embodiments.

FIG. 1 illustrates an exemplary surgical clip applier (10). As shown, surgical clip applier (10) generally includes a housing (12) having a stationary handle (14) and a movable handle or trigger (16) that is pivotally coupled to housing (12). A shaft assembly (18) extends from housing (12) and includes a pair of opposing jaws (20) formed on a distal end thereof for crimping a surgical clip. Shaft assembly (18) may be rotatably coupled to housing (12), and it may include a rotation knob (22) for rotating shaft assembly (18) relative to housing (12).

Figure 2:
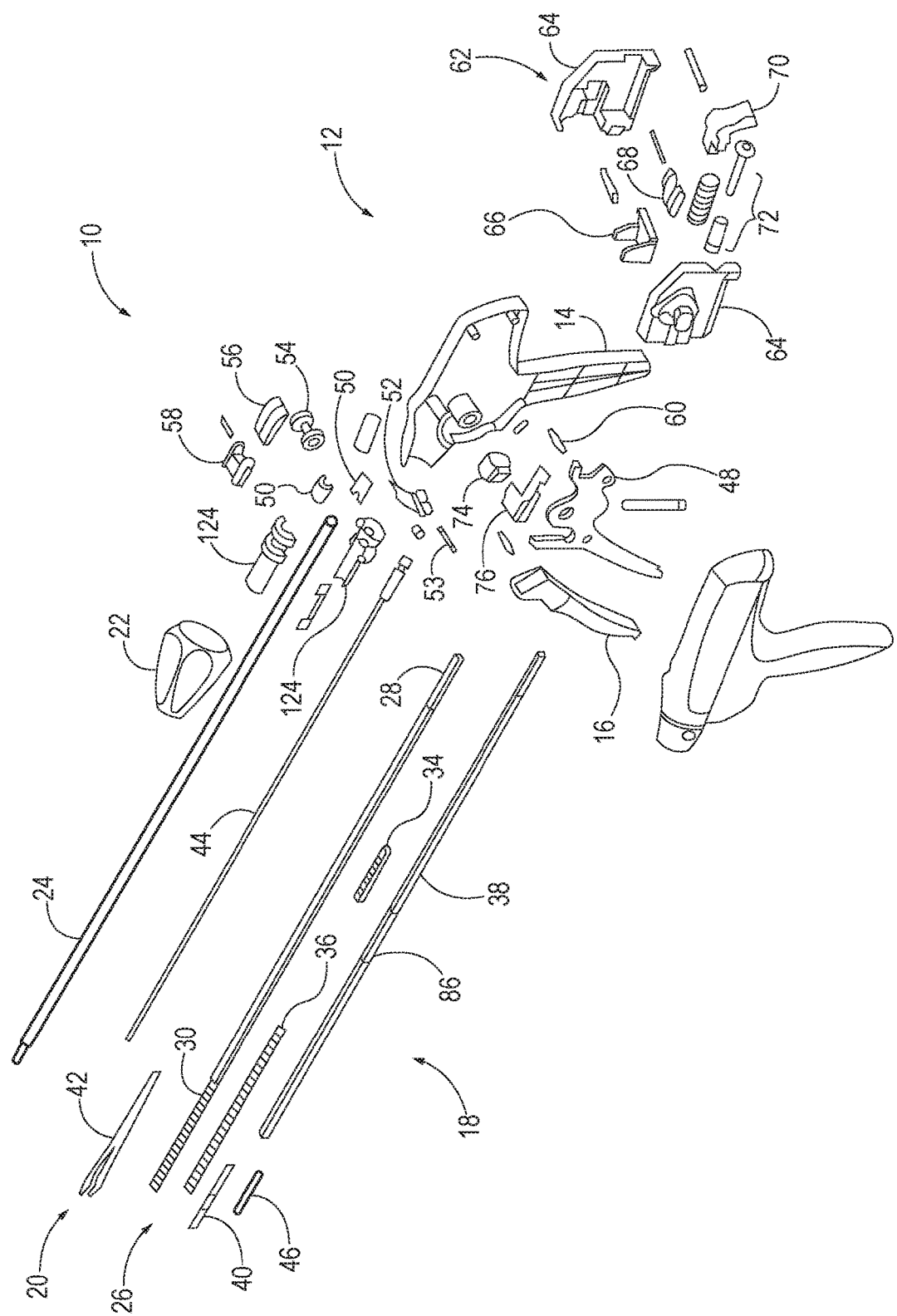
FIG. 2 depicts an exploded view of the surgical clip applier of FIG. 1.

FIG. 2 illustrates an exploded view of surgical clip applier (10) shown in FIG. 1, and the various components will be described in more detail below. As shown, a clip advancing assembly includes a trigger insert (48) that is coupled to trigger (16), a feed bar coupler (50) that mates to a feed bar (38), and a feed link (52) that is adapted to extend between trigger insert (48), and feed bar coupler (50) for transferring motion from trigger insert (48) to feed bar coupler (50). Closure link roller (54) is slidably coupled to trigger insert (48). Closure link (56) is adapted to couple to closure link roller (54), and a closure coupler (58) is adapted to couple to closure link (56) and to a push rod (44). Shaft (53) may be adapted to pivotally rotate within a recess of trigger insert (48). A pawl (60) is adapted to be rotatably disposed within housing (12). As shown, overload mechanism (62) includes an overload housing (64) formed from two halves (64a-b) and containing a profile link (66), a toggle link (68), a pivot link (70), and a biasing assembly (72). A clip quantity indicator has an indicator wheel (74) and an indicator actuator (76).

FIGS. 3A-6 illustrate examples of the various components of shaft assembly (18) of surgical clip applier (10). As shown in FIG. 2, shaft assembly (18) includes an outer tube (24) that houses the shaft components, which may include a jaw retaining assembly (26) having a jaw retainer shaft (28) with a clip track (30) and a push rod channel (not shown) formed thereon. Jaws (20) may be configured to mate to a distal end of clip track (30). Shaft assembly (18) may also include a clip advancing assembly, which in the present example includes a feeder shoe (34) that is adapted to be slidably disposed within clip track (30) to advance a series of clips (36) positioned therein; and a feed bar (38) that is adapted to drive feeder shoe (34) through clip track (30).

Feed bar (38) may include an advancer assembly (40) that is adapted to mate to a distal end thereof for advancing a distal-most clip into jaws (20). Feed bar (38) may also include a feature to control the amount of movement of feed bar (38) relative to clip track (30). Such a configuration may ensure that feeder shoe (34) is advanced a predetermined distance each time trigger (16) is actuated, thereby advancing only a single clip into jaws (20). While a variety of techniques can be used to control the distal of movement of feed bar (38), in the present example, feed bar (38) may include a protrusion formed thereon that is adapted to be slidably received within a corresponding slot (88) (FIG. 3B) formed in jaw retainer shaft (28). The length of slot (88) is effective to limit movement of the protrusion therein, thus limiting movement of feed bar (38). Accordingly, in use, feed bar (38) can slide between a fixed proximal position and a fixed distal position with respect to the clip track (30), thereby allowing feed bar (38) to advance feeder shoe (34) by a predetermined distance with each advancement of feed bar (38).

Shaft assembly (18) may also include a clip forming or camming assembly, which in the present example includes a cam (42) that is adapted to slidably mate to jaws (20); and push rod (44) that couples to cam (42) to move cam (42) relative to jaws (20). Shaft assembly (18) may also include a tissue stop (46) that may mate to a distal end of clip track (30) for facilitating positioning of jaws (20) relative to a surgical site. Clip track (30) may also include several openings (30c) formed therein for receiving a tang (not shown) formed on feeder shoe (34) adapted to be disposed within clip track (30). Surgical clip applier (10) also includes a shaft coupler (124). Clip track (30) may also include a stop tang (118) (shown in FIG. 3B) formed thereon.

The various components of one exemplary clip advancing assembly are shown in more detail in FIGS. 3A-4. Referring first to FIGS. 3A-3C, jaw retaining assembly (26) is shown to include an elongate substantially planar jaw retainer shaft (28) having a proximal end (28a) that mates to outer tube (24); and a distal end (28b) that is adapted to mate to jaws (20). A variety of structures and techniques may be used to mate proximal end (28a) of jaw retainer shaft (28) to outer tube (24). As shown, proximal end (28a) includes teeth (31) formed on opposing sides thereof that are adapted to be received within corresponding holes or openings (not shown) formed in outer tube (24); and a cut-out (29) formed therein that allows the opposing sides of proximal end (28a) to deflect or to form a spring. Cut-out (29) allows the opposing sides of proximal end (28a) of jaw retainer shaft (28) to be compressed toward one another when jaw retainer shaft (28) is inserted in outer tube (24). Once teeth (31) are aligned with the corresponding openings in outer tube (24), proximal end (28a) of jaw retainer shaft (28) will return to its original, uncompressed configuration thereby causing teeth (31) to extend into the corresponding openings to engage outer tube (24).

A variety of structures and techniques may also be used to mate distal end (28b) of jaw retainer shaft (28) to jaws (20). As shown, distal end (28b) of jaw retainer shaft (28) includes several cut-outs or teeth (78) formed therein for mating with corresponding protrusions or teeth (94) formed on jaws (20), which will be discussed in more detail below with respect to FIG. 5. Teeth (78) allow a proximal portion of jaws (20) to be substantially co-planar with jaw retainer shaft (28).

As shown, jaw retaining assembly (26) includes a push rod channel (32) formed thereon for slidably receiving push rod (44), which is used to advanced cam (42) over jaws (20). Push rod channel (32) may be formed using a variety of techniques; and may have any shape and size depending on the shape and size of push rod (44). As shown in FIG. 4, push rod channel (32) is fixedly attached, e.g., by welding, to a superior surface of jaw retainer shaft (28), and it has a substantially rectangular shape and defines a pathway (32a) extending therethrough. Push rod channel (32) may also extend along all or only a portion of jaw retainer shaft (28). A person skilled in the art will appreciate that jaw retaining assembly (26) does not need to include a push rod channel (32) for facilitating movement of push rod (44) within shaft assembly (18) of surgical clip applier (10).

As shown in FIGS. 3A-4, jaw retaining assembly (26) includes clip track (30) mated thereto or formed thereon. Clip track (30) is shown mated to an inferior surface of jaw retainer shaft (28). Clip track (30) extends distally beyond distal end (28b) of jaw retainer shaft (28) to allow a distal end (30b) of clip track (30) to be substantially aligned with jaws (20). In use, clip track (30) is configured to seat at least one, and preferably a series, of clips therein. Accordingly, clip track (30) includes opposing side rails (80a-b) that are adapted to seat opposing legs of one or more clips therein, such that the legs of the clips are axially aligned with one another. In some versions, clip track (30) may be configured to seat about twenty clips that are pre-disposed within clip track (30) during manufacturing. A person skilled in the art will appreciate that the shape, size, and configuration of clip track (30) may vary depending on the shape, size, and configuration of clips, or other closure devices such as staples, adapted to be received therein. Moreover, a variety of other structures and techniques may be used, instead of clip track (30), to retain a clip supply with shaft assembly (18).

Figure 5:
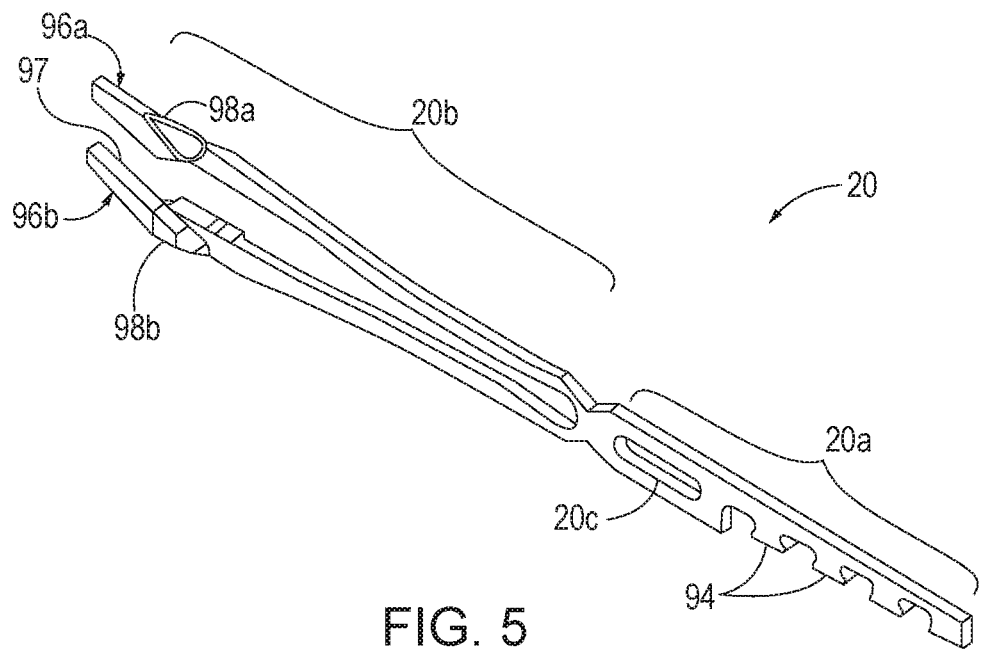
FIG. 5 depicts a perspective view of first and second opposing jaws of the surgical clip applier shown in FIG. 1.
Figure 6:
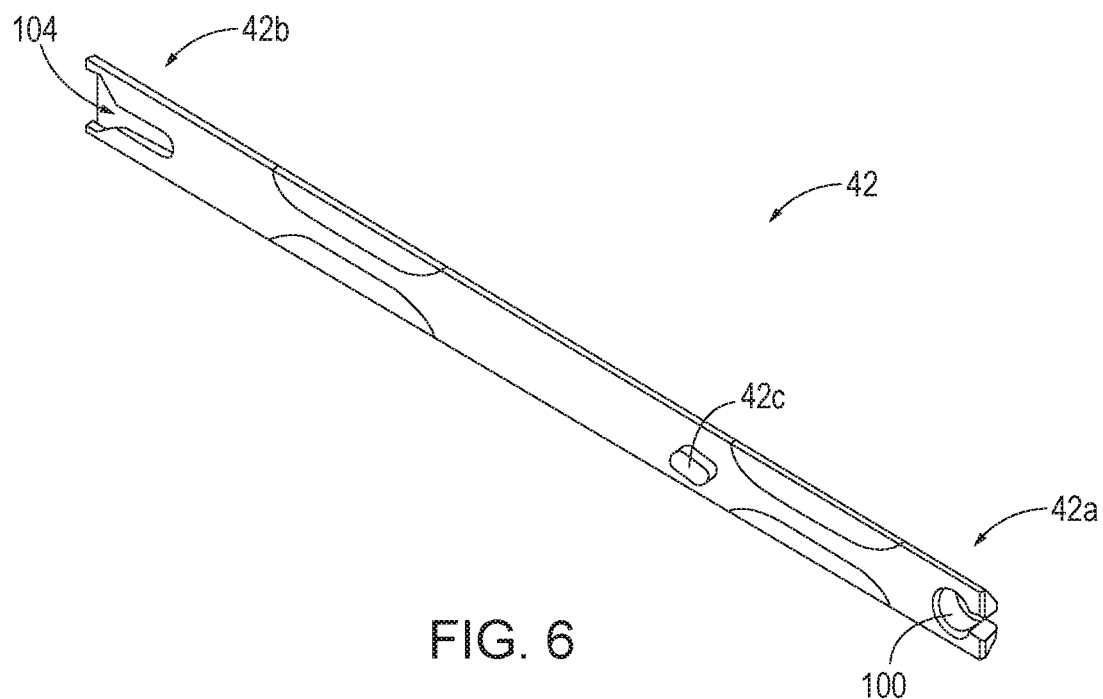
FIG. 6 depicts a perspective view of a cam for use with the jaws shown in FIG. 5.

FIGS. 5-6 illustrate various exemplary components of a clip forming assembly. FIG. 5 shows an example of jaws (20). As previously discussed, jaws (20) may include a proximal portion (20a) having teeth (94) for mating with corresponding teeth (78) formed on jaw retainer shaft (28). Other structures and techniques may, however, be used to mate jaws (20) to jaw retainer shaft (28). For example, a dovetail connection, a male-female connection, etc., may be used. Alternatively, jaws (20) may be integrally formed with jaw retainer shaft (28). Distal portion (20b) of jaws (20) may be adapted to receive a clip therebetween; and thus distal portion (20b) may include first and second opposing jaws (96a-b) that are movable relative to one another. In the present example, jaws (96a-b) are biased to an open position, and a force is required to move jaws (96a-b) toward one another. Jaws (96a-b) may each include a groove formed therein on opposing inner surfaces thereof for receiving the legs of a clip in alignment with jaws (96a-b). Jaws (96a-b) may also each include a cam track (98a-b) formed therein for allowing cam (42) to engage jaws (96a-b) and move jaws (96a-b) toward one another. In the present example, cam track (98a-b) is formed on a superior surface of jaws (96a-b).

FIG. 6 illustrates an exemplary cam (42) for slidably mating to and engaging the jaws (96a-b). Cam (42) may have a variety of configurations, but as shown, cam (42) includes a proximal end (42a) that is adapted to mate to a push rod (44), and a distal end (42b) that is adapted to engage jaws (96a-b). A variety of structures and techniques may be used to mate cam (42) to push rod (44); but in the present example, cam (42) includes a female or keyed cut-out (100) formed therein and adapted to receive a male or key member (not shown) formed on a distal end (44b) of push rod (44). A person skilled in the art will appreciate that cam (42) and push rod (44) may optionally be integrally formed with one another. A proximal end (44a) of push rod (44) may be adapted to mate to a closure link assembly, for moving push rod (44) and cam (42) relative to jaws (20). As is further shown in FIG. 6, cam (42) may also include a protrusion (42c) formed thereon that is adapted to be slidably received within an elongate slot (20c) formed in jaws (20). In use, protrusion (42c) and slot (20c) may function to form a proximal stop for the clip forming assembly. Distal end (42b) of cam (42) may be adapted to engage jaws (96a-b). While a variety of structures and techniques may be used, in the present example, distal end (42b) includes a camming channel or tapering recess (104) formed therein for slidably receiving cam tracks (98a-b) on jaws (96a-b).

As shown in FIGS. 7 and 8, cam (42) may be advanced from a proximal position, in which jaws (96a-b) are spaced a distance (D) apart from one another, to a distal position, in which jaws (96a-b) are positioned adjacent to one another and in a closed position. As cam (42) is advanced over jaws (96a-b), tapering recess (104) pushes jaws (96a-b) toward one another, thereby crimping a clip disposed therebetween.

II. EXEMPLARY JAW RETAINING ASSEMBLIES

As previously described, surgical instrument (10) generally includes housing (12) having stationary handle (14) and movable handle or trigger (16) that is pivotally coupled to housing (12). Shaft assembly (18) extends distally from housing (12). Shaft assembly (18) may be rotatably coupled with housing (12) and may include rotation knob (22) for rotating shaft assembly (18) relative to housing (12). As will be described in greater detail below, surgical instrument (10) also includes a jaw retaining assembly (210, 310, 410, 510, 610, 710, 810, 910). As will be described with respect to the examples, jaw retaining assembly (210, 310, 410, 510, 610, 710, 810, 910) includes at least a first metallic portion (212, 312, 412, 512, 612, 712, 812, 912) and a second metallic portion (214, 314, 414, 514, 614, 714, 814, 914). Jaw retaining assembly (210, 310, 410, 510, 610, 710, 810, 910) includes a first and second opposing jaws (216a-b, 316a-b, 416a-b, 516a-b, 616a-b, 716a-b, 816a-b, 916a-b) for crimping a surgical clip (36) (shown in FIG. 7A) that extend distally from a jaw retainer shaft (218) or a shaft (318, 418, 518, 618a-b, 718, 818, 918).

A. First Exemplary Jaw Retaining Assembly

FIGS. 8-13 show a first exemplary jaw retaining assembly (210) as including first and second metallic portions (212, 214). Jaw retaining assembly (210) is functionally similar to jaw retaining assembly (26) described above. Jaw retaining assembly (210) additionally includes first and second opposing jaws (216a-b) coupled with a jaw retainer shaft (218). Jaw retainer shaft (218) is functionally similar to jaw retainer shaft (28) described above. As shown, jaw retainer shaft (218) includes a proximal portion (220) and a distal portion (222). Distal portion (222) is shown in greater detail in FIG. 9, while proximal portion (220) is shown in greater detail in FIG. 11. As shown in FIG. 8, jaw retainer shaft (218) includes a slot (224) having a similar structure and function to slot (88) shown and described in FIG. 3B.

As shown in FIG. 9, jaw retainer shaft (218) includes first and second arms (226, 228) extending distally from a fork point (230) of jaw retainer shaft (218). Fork point (230) separates first and second arms (226, 228). It is desirable that fork point (230) be sufficiently flexible to allow for first and second jaws (216a-b) to move relative to one another. Conversely, at least first and second clip contact surfaces (232a-b) of first and second jaws (216a-b) are desirably rigid and are not intended to significantly deform. This rigidity of first and second clip contact surfaces (232a-b) allows for improved clip control during clip advancement.

Figure 10:
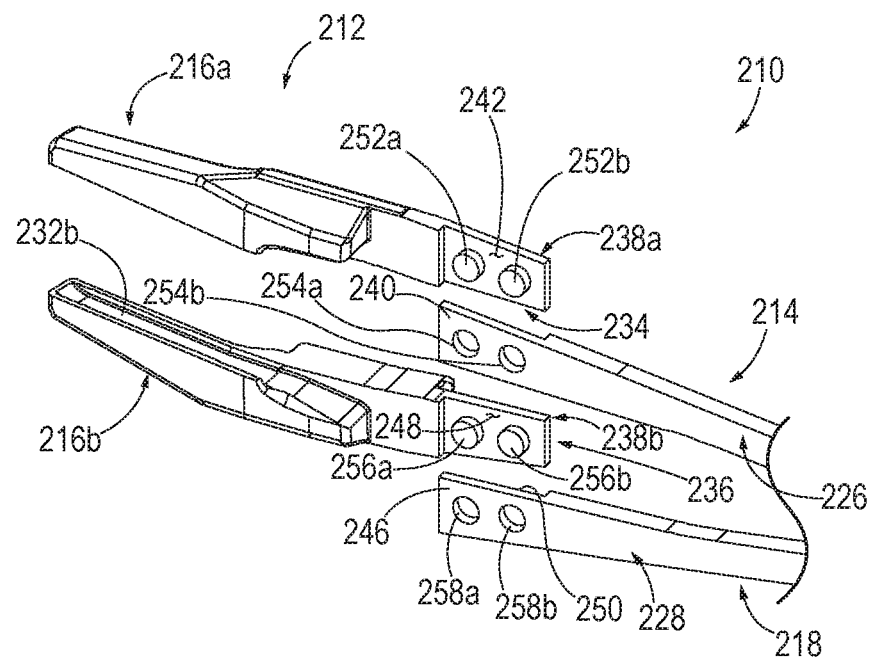
FIG. 10 depicts an enlarged exploded perspective view of a distal portion of the jaw retaining assembly of FIG. 9.

FIG. 10 shows an enlarged exploded perspective view of distal portion (222) of jaw retaining assembly (210). A method of manufacturing a surgical instrument, such as surgical clip applier (10), that is configured to apply surgical clip (36) to a patient is now described with reference FIG. 10. The method includes metal injection molding first metallic portion (212) of jaw retaining assembly (210). As used herein, metal injection molding (MIM) is intended to refer to any metalworking process where finely-powdered metal is mixed with a binder material to create a feedstock that is subsequently shaped and solidified using molding process (such as injection molding). MIM allows for high volume, complex parts to be shaped using only a single step. As shown in FIGS. 8-10 and 12-13, first metallic portion (212) includes opposing first and second jaws (216a-b). It is desirable that first and second clip contact surfaces (232a-b) of first and second opposing jaws (216a-b) be formed through a MIM process.

With continued reference to FIG. 10, second metallic portion (214) of jaw retaining assembly (210) is formed by MIM, stamping, and/or laser cutting. Second metallic portion (214) is separately formed from first metallic portion (212). Second metallic portion (214) includes jaw retainer shaft (218). For example, jaw retainer shaft (218) may be stamped from a material using a conventional stamping process.

Figure 12:
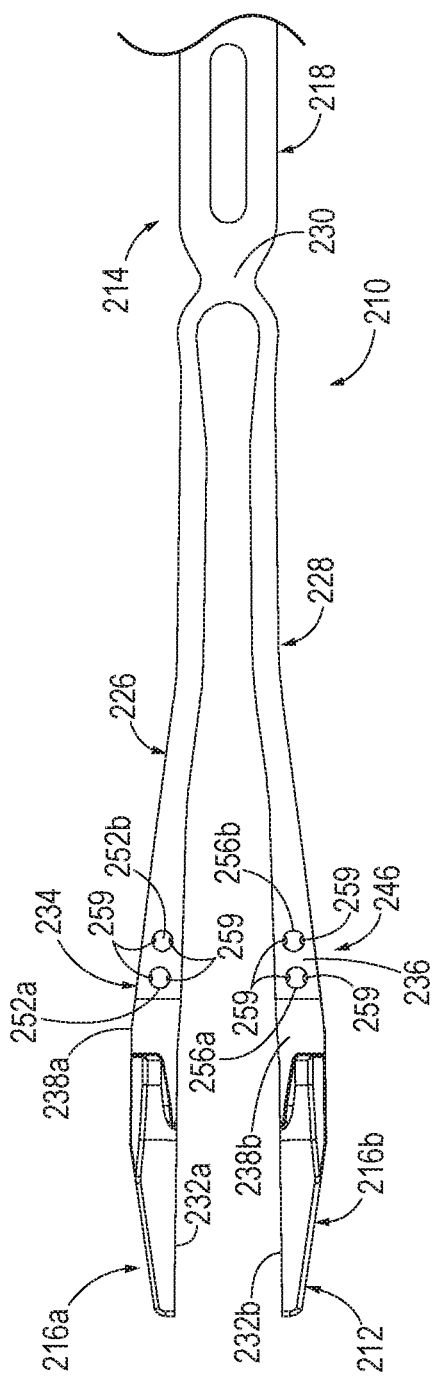
FIG. 12 depicts a top view of the distal portion of the jaw retaining assembly of FIG. 9.

As shown in FIGS. 10 and 12, to aid in the coupling of first and second metallic portions (212, 214), one or more coupling features may be included. First jaw (216a) is fixably coupled with first arm (226) at a first joint (234), shown as a lap joint. Similarly, second jaw (216b) is fixably coupled with second arm (228) at a second joint (236), shown as another lap joint. First joint (234) is disposed proximal to first clip contact surface (232a) of first jaw (216a) and distal to fork point (230) that separates first and second arms (226, 228). Second joint (236) is disposed proximal to a second clip contact surface of second jaw (216b) and distal to fork point (230) that separates first and second arms (226, 228). First and second clip contact surfaces (232a-b) of respective first and second jaws (216a-b) are configured to contact surgical clip (36).

With continued reference to FIGS. 10 and 12, first joint (234) is disposed adjacent a proximal end (238a) of first jaw (216a) and a distal end (240) of first arm (226). More specifically, an interior surface (242) of proximal end (238a) of first jaw (216a) is disposed against an interior surface (244) of distal end (240) of first arm (226). Similarly, second joint (236) is adjacent proximal end (238b) of second jaw (216b) and a distal end (246) of second arm (228). More specifically, an interior surface (248) of proximal end (238b) of second jaw (216b) is disposed against an interior surface (250) of distal end (240) of second arm (228).

As shown in FIG. 10, first and second pins (252a-b) extend from interior surface (242) of proximal end (238a) of first jaw (216a). First and second pins (252a-b) are fixably coupled with first and second corresponding recesses (254a-b) formed in interior surface (244) of distal end (240) of first arm (226). Similarly, third and fourth pins (256a-b) extend from interior surface (248) of proximal end (238b) of second jaw (216b). Third and fourth pins (256a-b) are fixably coupled with third and fourth corresponding recesses (258a-b) formed in interior surface (250) of distal end (246) of second arm (228).

As shown, the method also includes fixably coupling first and second metallic portions (212, 214) of jaw retaining assembly (210) together. For example, first and second metallic portions (212, 214) may be fixably coupled together using a variety of different methods, including using one or more coupling features and/or welding. A MIM process may be used to create the entire first and second jaws (216a-b) and stamping may be used to impart pin stamped features that enhance welding. Welding first and second opposing jaws (216a-b) using exemplary welds (259) (shown in FIG. 12) to a stamped or laser cut jaw retainer shaft (218) that includes fork point (230), serving as a proximal spring feature, provides improved support and control of surgical clip (36).

Figure 11:
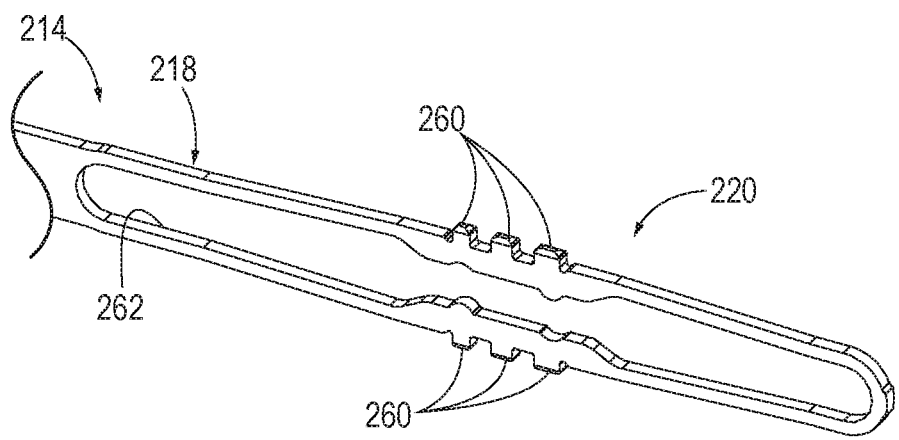
FIG. 11 depicts an enlarged view of a proximal portion of the jaw retaining assembly of FIG. 8.

FIG. 11 shows an enlarged view of a proximal portion of jaw retaining assembly (210) of FIG. 8. As previously described with respect to FIG. 2, proximal portion (220) of jaw retainer shaft (218) includes teeth (260) formed on opposing outer sides. Teeth (260) are configured to be received within corresponding holes or openings formed in outer tube (24), and a cut-out (262) formed therein that allows the opposing sides of proximal portion (220) of jaw retainer shaft (218) to deflect or to form a spring.

Figure 13:
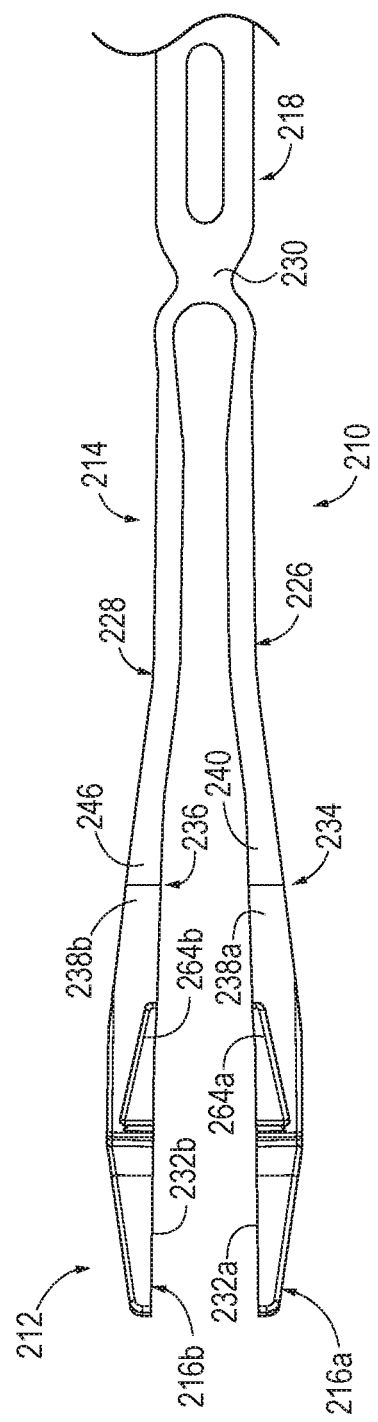
FIG. 13 depicts a bottom view of the distal portion of the jaw retaining assembly of FIG. 12.
Figure 39:
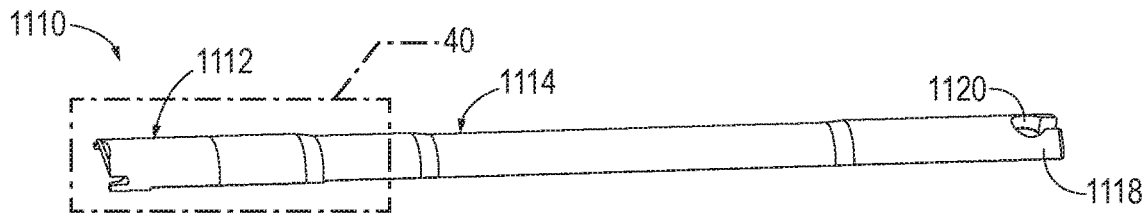
FIG. 39 depicts a front perspective view of a second exemplary cam including proximal and distal portions.
Figure 40:
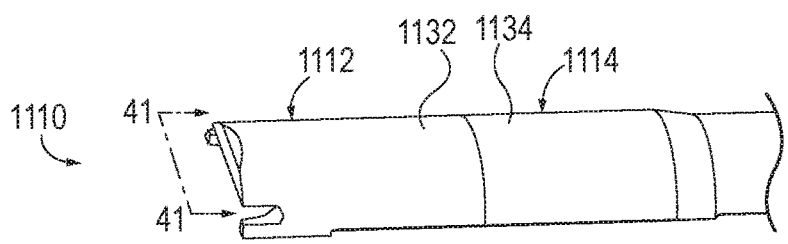
FIG. 40 depicts an enlarged front perspective view of the cam of FIG. 39.

FIG. 12 shows a top view of the distal portion of jaw retaining assembly (210), while FIG. 13 shows a bottom view of distal portion (222) of jaw retaining assembly (210). First and second jaws (216a-b) may also each include a cam track (264a-b) for allowing cam (shown in FIGS. 6, 32, and 39) to engage first and second jaws (216a-b) and move first and second jaws (216a-b) toward one another. In an exemplary embodiment, cam tracks (264a-b) are formed on a superior surface of first and second jaws (216a-b).

B. Second Exemplary Jaw Retaining Assembly

Figure 14A:
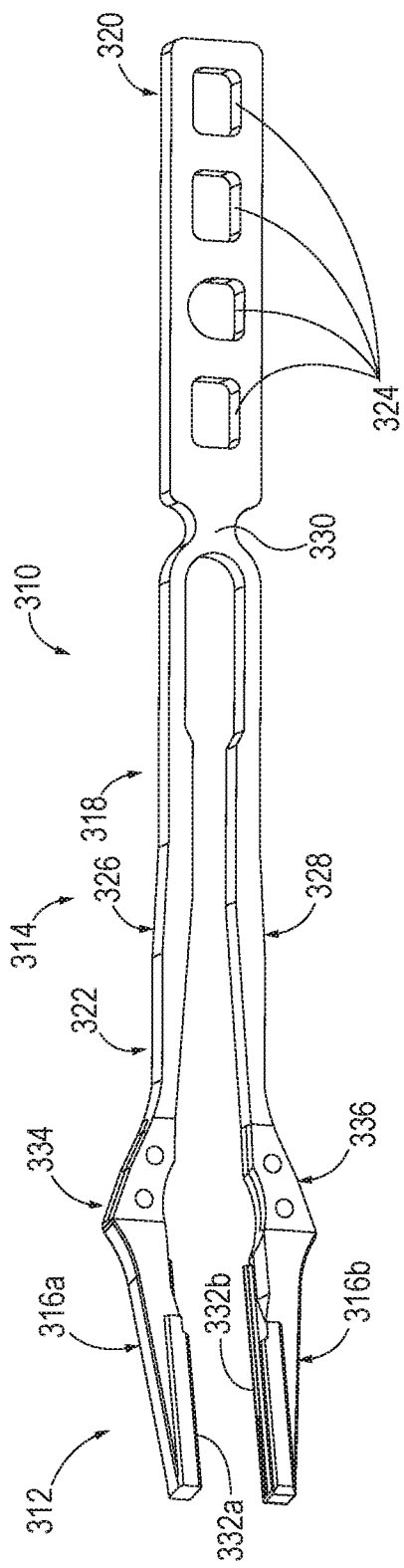
FIG. 14A depicts a front perspective view of a second exemplary jaw retaining assembly including first and second opposing jaws and a shaft.

FIGS. 14A-17 show a second exemplary jaw retaining assembly (310) as including first and second metallic portions (312, 314). Jaw retaining assembly (310) includes opposing first and second jaws (316a-b) coupled with shaft (318). As shown, shaft (318) includes a proximal portion (320) and a distal portion (322). Distal portion (322) is shown in greater detail with respect to FIG. 15. As shown in FIGS. 14A-14B, shaft (318) includes a plurality of apertures (324) having function to protrusions or teeth (94) shown and described with respect to FIG. 5.

Figure 14B:
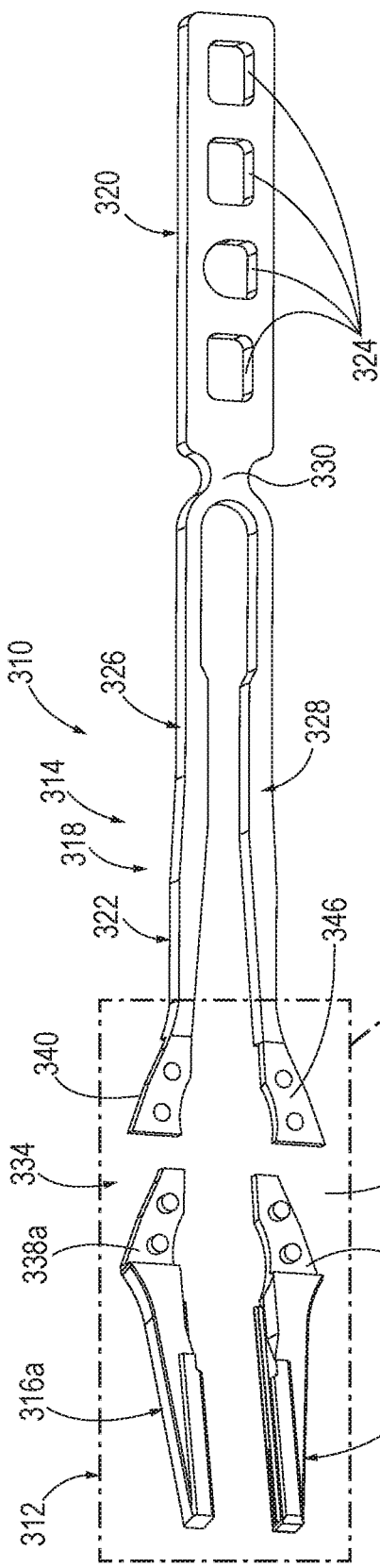
FIG. 14B depicts an exploded front perspective view of the jaw retaining assembly of FIG. 14A.

As shown in FIGS. 14A-14B, shaft (318) includes first and second arms (326, 328) extending distally from a fork point (330) of shaft (318). Fork point (330) separates first and second arms (326, 328). It is desirable that fork point (330) to be sufficiently flexible to allow for first and second jaws (316a-b) to move relative to one another. Conversely, at least first and second clip contact surfaces (332a-b) of first and second jaws (316a-b) are desirably rigid and are not intended to significantly deform. This rigidity of at least first and second clip contact surfaces (332a-b) allows for improved clip control during clip advancement.

Figure 15:
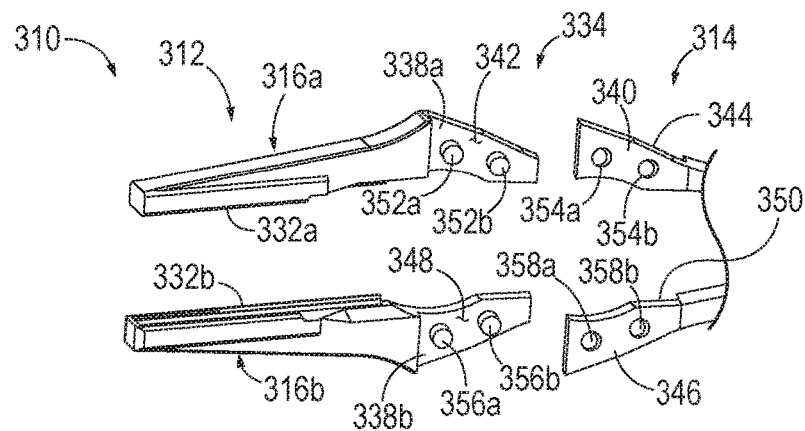
FIG. 15 depicts an enlarged perspective view of a portion of the jaw retaining assembly of FIG. 14A including the first and second opposing jaws and the shaft of FIG. 14B.

FIG. 15 shows an enlarged exploded perspective view of distal portion (322) of jaw retaining assembly (310). A method of manufacturing a surgical instrument, such as surgical clip applier (10), that is configured to apply surgical clip (36) to a patient is now described with respect FIG. 15. The method includes metal injection molding first metallic portion (312) of jaw retaining assembly (310). As shown, first metallic portion (312) includes first and second jaws (316a-b). It is desirable that at least first and second clip contact surfaces (332a-b) of first and second opposing jaws (316a-b) be formed through a MIM process. Second metallic portion (314) of jaw retaining assembly (310) is metal injection molding, stamping and/or laser cutting. Second metallic portion (314) is separately formed from first metallic portion (312). Second metallic portion (314) includes shaft (318). For example, shaft (318) may be stamped according to an exemplary embodiment.

As shown in FIGS. 14B-15, to aid in the coupling of first and second metallic portions (312, 314), one or more coupling features may be included. First jaw (316a) is fixably coupled with first arm (326) at a first joint (334), shown as a lap joint. Similarly, second jaw (316b) is fixably coupled with second arm (328) at a second joint (336), shown as another lap joint. While lap joints, are shown, a variety of other joints may also be used including butt joints. First joint (334) is disposed proximal to first clip contact surface (332a) of first jaw (316a) and distal to fork point (330) that separates first and second arms (326, 328). Second joint (336) is disposed proximal to second clip contact surface (332b) of second jaw (316b) and distal to fork point (330) that separates first and second arms (328, 330). First and second clip contact surfaces (332a-b) of respective first and second jaws (316a-b) are configured to contact surgical clip (36).

As shown, first joint (334) is adjacent a proximal end (338a) of first jaw (316a) and a distal end (340) of first arm (326). More specifically, an interior surface (342) of proximal end (338a) of first jaw (316a) is disposed against an interior surface (344) of distal end (340) of first arm (326). Similarly, second joint (336) is adjacent proximal end (338b) of second jaw (316b) and a distal end (346) of second arm (328). More specifically, an interior surface (348) of proximal end (338b) of second jaw (316b) is disposed against an interior surface (350) of distal end (340) of second arm (328).

As shown in FIG. 15, first and second pins (352a-b) extend from interior surface (342) of proximal end (338a) of first jaw (316a). First and second pins (352a-b) are fixably coupled with first and second corresponding recesses (354a-b) formed in interior surface (344) of distal end (340) of first arm (326). Similarly, third and fourth pins (356a-b) extend from interior surface (348) of proximal end (338b) of second jaw (316b). Third and fourth pins (356a-b) are fixably coupled with corresponding third and fourth recesses (358a-b) formed in interior surface (350) of distal end (346) of second arm (328).

Figure 16:
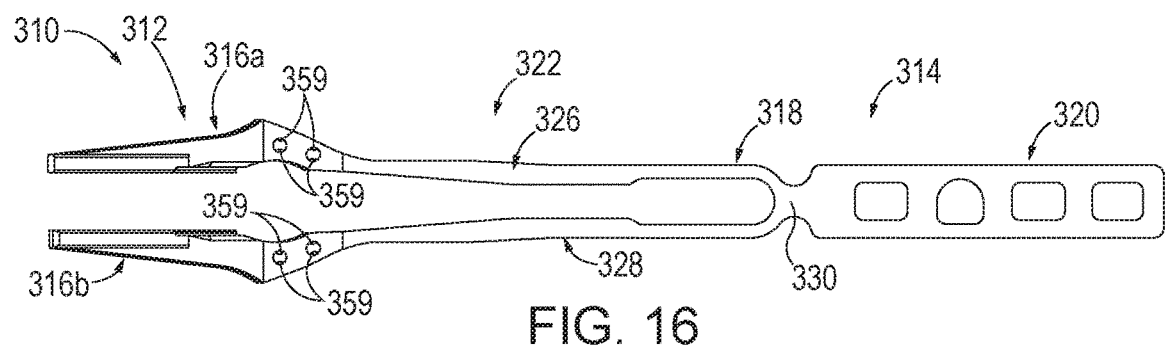
FIG. 16 depicts a top view of the jaw retaining assembly of FIG. 14A.
Figure 17:
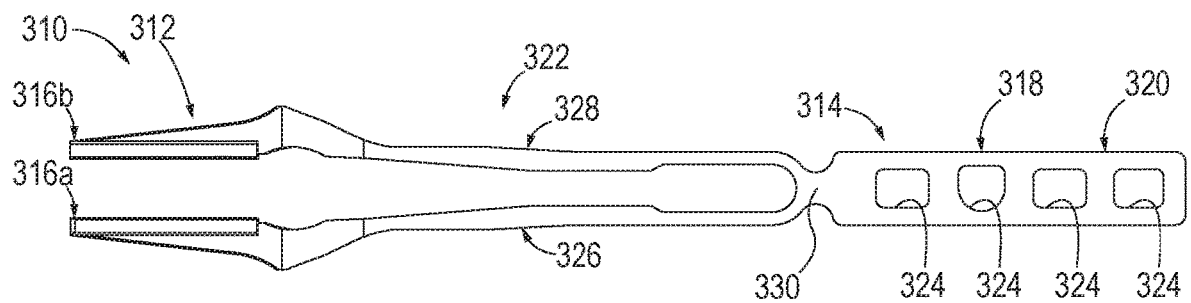
FIG. 17 depicts a bottom view of the jaw retaining assembly of FIG. 14A.

As shown, the method also includes fixably coupling first and second metallic portions (312, 314) of jaw retaining assembly (310) together. For example, first and second metallic portions (312, 314) may be fixably coupled together using a variety of different methods, including using one or more coupling features and/or welding. As shown, MIM process is used to create the entire first and second jaws (316a-b) and pin stamped features allow for welding together. Welding first and second jaws (316a-b) to a stamped or laser cut shaft (318) using welds (359) (shown in FIG. 16) provides improved clip support and control, while allowing fork point (330) to act as a proximal spring feature. FIG. 16 shows a top view of distal portion (322) of shaft (318), while FIG. 17 shows a bottom view of distal portion (322) of shaft (318).

C. Third Exemplary Jaw Retaining Assembly

Figure 18:
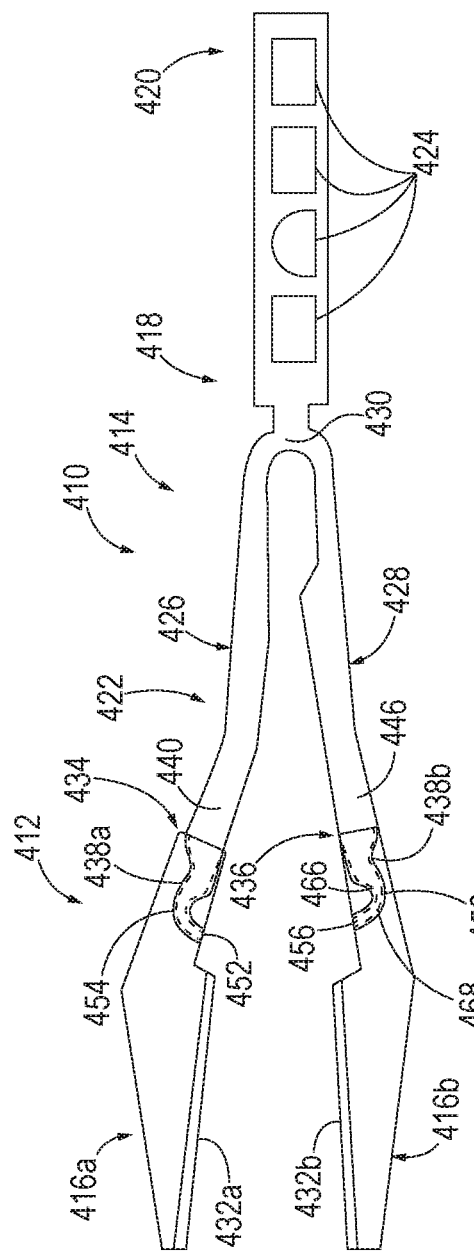
FIG. 18 depicts a front view of a third exemplary jaw retaining assembly including first and second opposing jaws and a shaft.

FIGS. 18-21 show a third exemplary jaw retaining assembly (410) as including first and second metallic portions (412, 414). Jaw retaining assembly (410) also includes first and second opposing jaws (416a-b) coupled with a shaft (418). As shown, shaft (418) includes a proximal portion (420) and a distal portion (422). As shown in FIG. 18, shaft (418) includes a plurality of apertures (424) having function to protrusions or teeth (94) shown and described with respect to FIG. 5.

As shown in FIG. 18, shaft (418) includes first and second arms (426, 428) extending distally from a fork point (430) of shaft (418). Fork point (430) separates first and second arms (426, 428). It is desirable that fork point (430) to be sufficiently flexible to allow for first and second jaws (416a-b) to move relative to one another. Conversely, at least first and second clip contact surfaces (432a-b) of first and second jaws (416a-b) are desirably rigid and are intended not to significantly deform. This rigidity of at least first and second clip contact surfaces (432a-b) allows for improved clip control during clip advancement.

Figure 19:
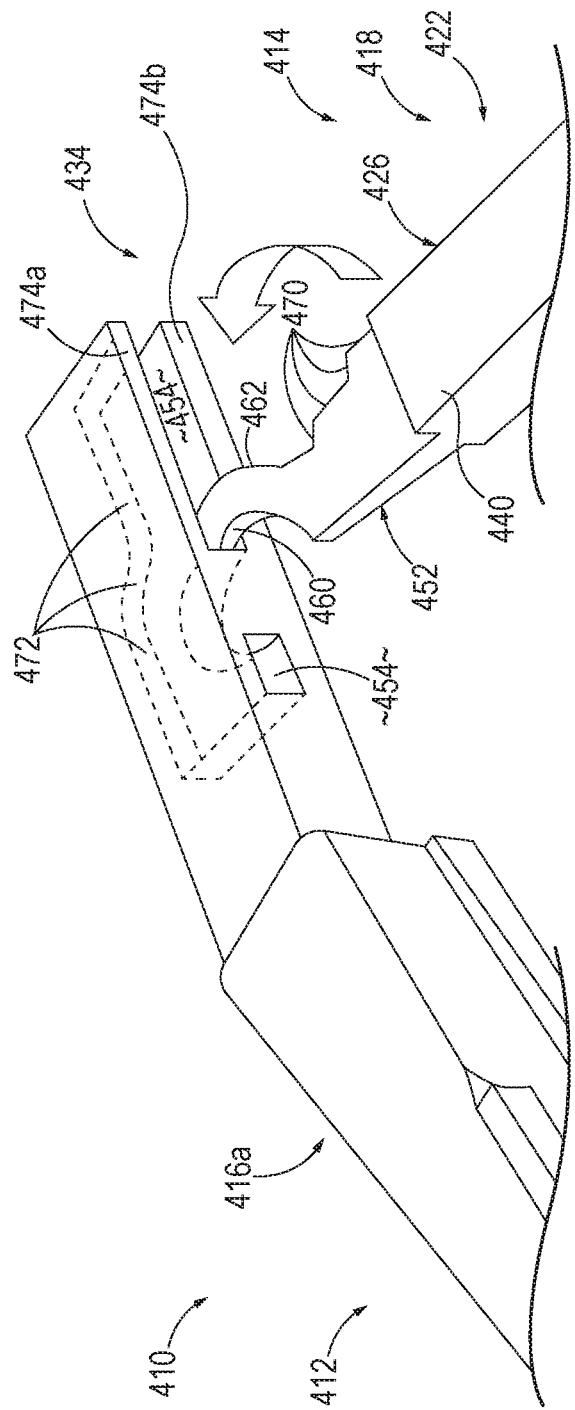
FIG. 19 depicts a perspective view of the jaw retaining assembly of FIG. 18, but as the shaft is being coupled with the first jaw.

A method of manufacturing a surgical instrument, such as surgical clip applier (10), that is configured to apply a surgical clip (36) to a patient is now described with respect FIGS. 18 and 19. FIG. 19 shows a perspective view of jaw retaining assembly (410) of FIG. 18 as shaft (418) is being actively coupled with first jaw (416a). The method includes metal injection molding first metallic portion (412) of jaw retaining assembly (410). As shown in FIGS. 18-21, first metallic portion (412) includes opposing first and second jaws (416a-b), that are separate from one another. It is desirable that at least first and second clip contact surfaces (432a-b) of first and second opposing jaws (416a-b) be formed through a MIM process. Second metallic portion (414) of jaw retaining assembly (410) is formed through metal injection molding, stamping and/or laser cutting. Second metallic portion (414) is separately formed from first metallic portion (412). Second metallic portion (414) includes shaft (418). For example, shaft (418) may be stamped.

First jaw (416a) is fixably coupled with first arm (426) at a first joint (434). Similarly, second jaw (416b) is fixably coupled with second arm (428) at a second joint (436). As shown, first joint (434) is adjacent a proximal end (438a) of first jaw (416a) and a distal end (440) of first arm (426). Similarly, second joint (436) is adjacent a proximal end (438b) of second jaw (416b) and a distal end (446) of second arm (428). First joint (434) is disposed proximal to first clip contact surface (432a) of first jaw (416a) and distal to fork point (430) that separates first and second arms (426, 428). Similarly, second joint (436) is disposed proximal to a second clip contact surface (432b) of second jaw (416b) and distal to fork point (430) that separates first and second arms (426, 428). First and second clip contact surfaces (432a-b) of respective first and second jaws (416a-b) are configured to contact surgical clip (36).

As shown in FIGS. 18-19, to aid in the coupling of first and second metallic portions (412, 414), one or more coupling features may be included. FIGS. 18-21 show first arm (426) as including a first arcuate hook (452) and second arm (428) as including a second arcuate hook (456). First and second arcuate hooks (452, 456) are configured to pivot into alignment with first and second recesses (454, 458) of respective first and second jaws (416a-b). As shown in FIGS. 18-21, first arcuate hook (452) extends from proximal end (438a) of first jaw (416a). First arcuate hook (452) is configured to be fixably coupled with first corresponding recess (454) of distal end (440) of first arm (426). Similarly, second arcuate hook (456) extends from proximal end (438b) of second jaw (416b). Second arcuate hook (456) is fixably coupled with second corresponding recess (458) of distal end (446) of second arm (428). FIG. 18 shows first arcuate hook (452) having an inner perimeter (460) and an outer perimeter (462), and second arcuate hook (456) having an inner perimeter (466) and an outer perimeter (468). Second arcuate hook (456) and second recess (458) have a similar structure (mirror image) and function to first arcuate hook (452) and first recess (454).

As shown in FIGS. 20 and 21 with respect to first arcuate hook (452), inner perimeter (460) of first arcuate hook (452) rotates around a cam surface (469) of first recess (454), shaped as a semicircle according to an exemplary embodiment. Outer perimeter (462) of first arcuate hook (452) may include one or more alignment features (470) configured to align and/or secure first arcuate hook (452) with one or more alignment features (472) of first corresponding recess (454). Additionally, as shown in FIGS. 19 and 20, first recess (454) is formed between first and second legs (474a-b) of proximal end (438a) of first jaw (416a).

FIG. 20 shows a side view of jaw retaining assembly of FIG. 18, with shaft (418) coupled with first jaw (416a-b). FIG. 21 shows a cross-sectional view of jaw retaining assembly (410) of FIG. 20 taken along line 21-21 of FIG. 20. As shown, the method also includes fixably coupling first and second metallic portions (412, 414) of jaw retaining assembly (410) together. For example, first and second metallic portions (412, 414) may be fixably coupled together using a variety of different methods, including using one or more coupling features and/or welding.

FIGS. 20 and 21 shows that when first arcuate hook (452) is fixably coupled with first recess (454), the exterior surfaces of first jaw (416a) and first arm (426) may appear flush and unobstructed. Additionally, with respect to FIG. 21, a distal end (476) of first arcuate hook (452) does not extend outside of first recess (454). While not shown, second arcuate hook (456) and second recess (458) function substantially similar to first arcuate hook (452) and first recess (454) described above. It is envisioned that the size and shape of first and second arcuate hooks (452, 456) and first and second corresponding recesses (454, 458) may vary. As shown in FIG. 20, first arcuate hook (452) is interleaved between first and second legs (474a-b) that define first recess (454).

MIM process to create the entire first and second jaws (416a-b) and pin stamped features that allow for welding together. Welding first and second opposing jaws (416a-b) to a stamped or laser cut shaft (418) including fork point (430) serving as a proximal spring feature, provides improved clip support and control. As shown in FIGS. 20 and 21, one or more welds (478) may be located along a weld zone (WZ).

D. Fourth Exemplary Jaw Retaining Assembly

Figure 22:
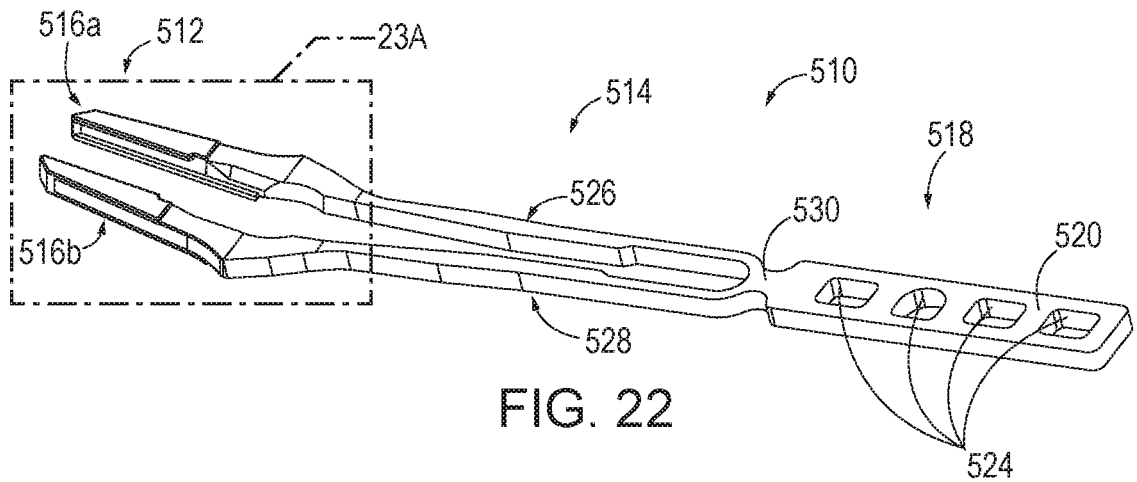
FIG. 22 depicts a front perspective view of a fourth exemplary jaw retaining assembly including first and second shoes.
Figure 23A:
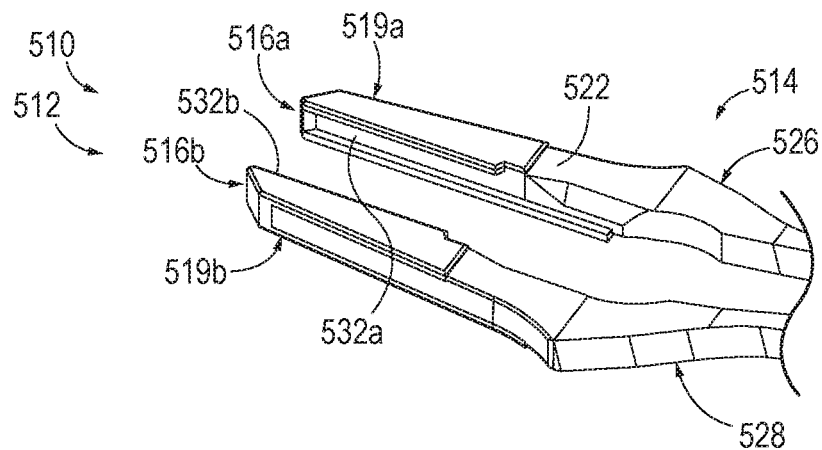
FIG. 23A depicts a front perspective view of an enlarged portion of the jaw retaining assembly of FIG. 22, with the first and second shoes coupled with first and second jaws.
Figure 23B:
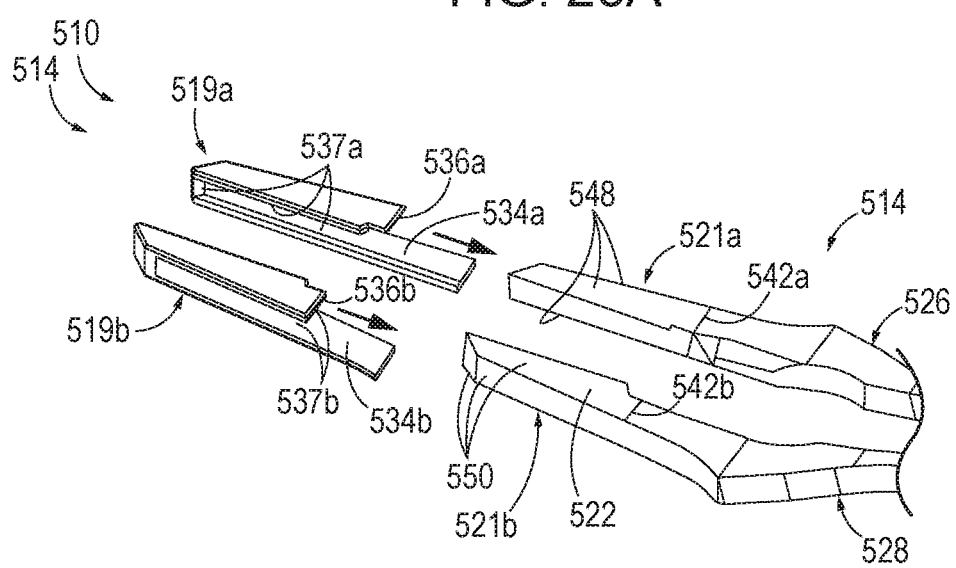
FIG. 23B depicts an exploded front perspective view of the jaw retaining assembly of FIG. 23A, but with the first and second shoes separated from the first and second jaws.

FIGS. 22-23B show a fourth exemplary jaw retaining assembly (510) that includes first and second metallic portions (512, 514). Jaw retaining assembly (510) includes first and second opposing jaws (516a-b) extending distally from a shaft (518). According to this exemplary embodiment, first metallic portion (512) include first and second opposing shoes (519a-b) that are fixably coupled with second metallic portion (514) that include first and second interior portions (521a-b) respective first and second jaws (516a-b) and shaft (518) extending proximally therefrom.

As shown in FIG. 22, shaft (518) includes a proximal portion (520) and a distal portion (522). As shown in FIG. 22, shaft (518) includes a plurality of apertures (524) having a similar function to protrusions or teeth (94) shown and described with respect to FIG. 5. As shown, shaft (518) includes first and second arms (526, 528) extending distally from a fork point (530) of shaft (518). Fork point (530) separates first and second arms (526, 528). It is desirable that fork point (530) to be sufficiently flexible to allow for first and second jaws (516a-b) to move relative to one another. Conversely, at least first and second clip contact surfaces (532a-b) of first and second jaws (516a-b) are rigid and are not intended to significantly deform. This rigidity of at least first and second clip contact surfaces (532a-b) allows for improved clip control during clip advancement.

A method of manufacturing a surgical instrument, such as surgical clip applier (10), that is configured to apply surgical clip (36) to a patient is now described with respect FIGS. 23A-23B. The method includes metal injection molding first metallic portion (512) of jaw retaining assembly (510). As shown in FIGS. 23A-23B, first metallic portion (512) includes first and second shoes (519a-b). It is desirable that at least first and second clip contact surfaces (532a-b) of first and second shoes (519a-b) be formed through a MIM process. Second metallic portion (514) of jaw retaining assembly (510) is formed by metal injection molding, stamping and/or laser cutting. Second metallic portion (514) is separately formed from first metallic portion (512). Second metallic portion (514) includes shaft (518) and interior portions (521a-b) of first and second jaws (516a-b). For example, second metallic portion (514) may be stamped from a material.

FIGS. 23A-23B show an enlarged view of distal portion (522) of jaw retaining assembly (510). More specifically, FIG. 23A shows a front perspective view of jaw retaining assembly (510) of FIG. 22, with first and second shoes (519a-b) coupled with first and second interior portions (521a-b), while FIG. 23B shows an exploded front perspective view of first and second shoes (519a-b) separated from first and second interior portions (521a-b) of first and second jaws (516a-b). FIG. 23B shows bottom portions (534a-b) of first and second shoes (519a-b) extending proximally beyond the rest of first and second shoes (519a-b). Additionally, as shown in FIG. 23B, first and second shoes (519a-b) may be thin walled shell members that generally surround first and second interior portions (521a-b).

With continued reference to FIGS. 23A-23B, the method also includes fixably coupling first and second metallic portions (512, 514) of jaw retaining assembly (510) together. For example, first and second metallic portions (512, 514) may be fixably coupled together using a variety of different methods, including using one or more coupling features and/or welding. As shown, to aid in the coupling of first and second metallic portions (512, 514), one or more coupling features may be included. First distal shoe (519a) includes a first distal stop (536a) and interior surface (537a), and second distal shoe (519b) includes a second distal stop (536b) and interior surfaces (537b). First interior portion (521a) includes a first alignment feature (542a). Similarly, second interior portion (521b) includes a second alignment feature (542b). First distal stop (536a) of first distal shoe (519a) is fixably coupled with first alignment feature (542a) of first jaw (516a). Similarly, second distal stop (536b) of second distal shoe (519b) is fixably coupled with second alignment feature (542b) of second jaw (516b). First distal shoe (519a) is aligned to at least partially surround at least three exterior walls (548) of interior portion (521a). Second distal shoe (519b) is aligned to at least partially surround at least three exterior walls (550) of second interior portion (521b).

As shown in FIGS. 23A-23B fixably coupling first distal shoe (519a) with first jaw (516a) includes welding interior surfaces (537a) of first distal shoe (519a) with exterior walls (548) of first interior portion (521a). Similarly, fixably coupling second distal shoe (519b) with second jaw (516b) includes welding interior surfaces (537b) of second distal shoe (519b) with exterior walls (550) of second interior portion (521b). A MIM process may be used to form the entire first and second jaws (516a-b), while stamping of second metallic portion (514) and accompanying stamped features allow suitably welding together. Welding first and second opposing jaws (516a-b) to a stamped or laser cut shaft (518) including fork point (530) serving as a proximal spring feature, provides improved clip support and control.

E. Fifth Exemplary Jaw Retaining Assembly

Figure 24A:
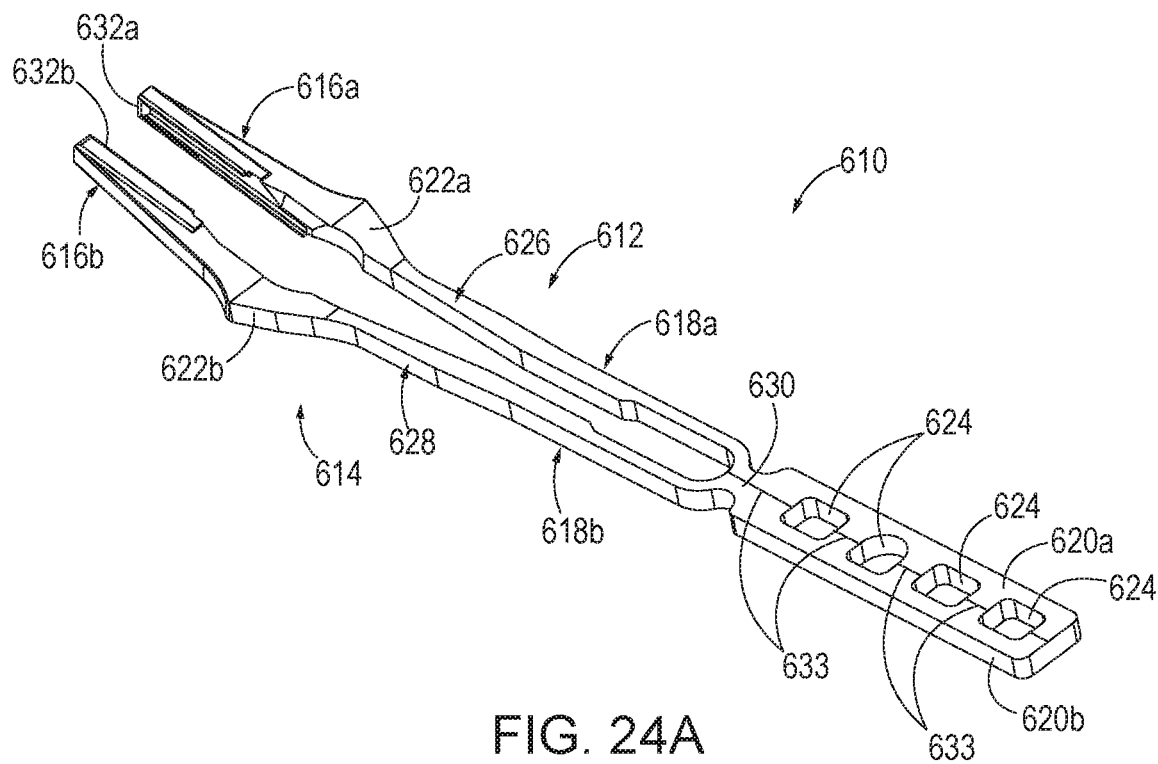
FIG. 24A depicts a front perspective view of a fifth exemplary jaw retaining assembly with first and second portions coupled together.
Figure 24B:
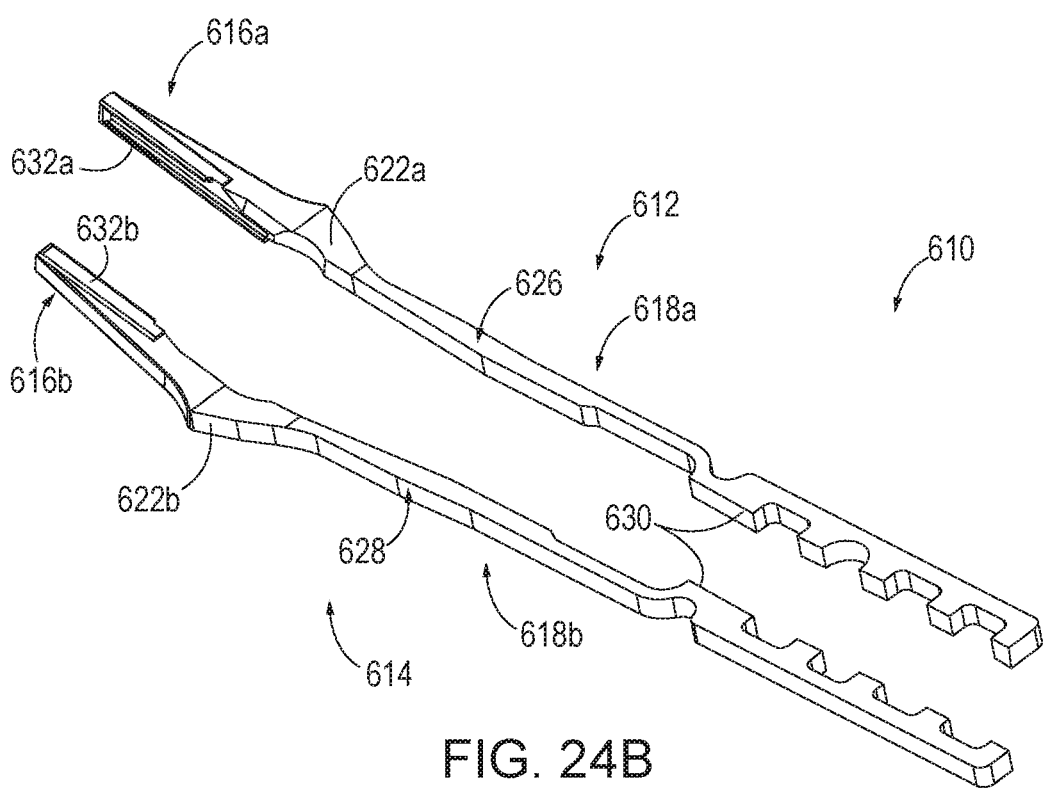
FIG. 24B depicts an exploded front perspective view of the jaw retaining assembly of FIG. 24A, but with the first and second portions separated from each other.

FIGS. 24A-24B show a fifth exemplary jaw retaining assembly (610) that includes first and second metallic portions (612, 614). Jaw retaining assembly (610) includes opposing first and second jaws (616a-b) that extend distally from respective first and second shafts (618a-b). As shown, first and second shafts (618a-b) each include a proximal portion (620a-b) and a distal portion (622a-b). FIG. 24A shows first and second metallic portions (612, 614) coupled together, while FIG. 24B shows first and second metallic portions (612, 614) separated from each other.

As shown, first shaft (618a) includes a first arm (626) extending distally from a fork point (630). Second shaft (618b) includes a second arm (628) extending distally from fork point (630). Fork point separates first and second arms (626, 628). It is desirable that fork point (630) be sufficiently flexible to allow for first and second jaws (616a-b) to move relative to one another. Conversely, at least first and second clip contact surfaces (632a-b) of first and second jaws (616a-b) are desirably rigid and are not intended to significantly deform. This rigidity of at least first and second clip contact surfaces (632a-b) allows for improved clip control during clip advancement. Shaft (618a-b) includes a plurality of apertures (624) that are formed by recesses in both first and second shafts (618a-b) having a similar function to protrusions or teeth (94) shown and described with respect to FIG. 5. According to this exemplary embodiment, first metallic portion (612) includes first jaw (616a), first arm (626), and proximal portion (620a). Similarly, second metallic portion (614) includes second jaw (616b), second arm (628), and proximal portion (620b). As shown, first and second metallic portions (612, 614) are mirror images of one another.

A method of manufacturing a surgical instrument, such as surgical clip applier (10), that is configured to apply surgical clip (36) to a patient is now described with respect FIGS. 24A-24B. The method includes metal injection molding first metallic portion (612) of jaw retaining assembly (610). As shown in FIGS. 24A-24B, first metallic portion (612) includes opposing first and second jaws (616a-b). It is desirable that at least first and second clip contact surfaces (632a-b) of first and second jaws (616a-b) be formed through a MIM process. With continued reference to FIG. 24A-24B, second metallic portion (614) of jaw retaining assembly (610) is formed by metal injection molding, stamping and/or laser cutting. Second metallic portion (614) is separately formed from first metallic portion (612).

As shown, the method also includes fixably coupling first and second metallic portions (612, 614) of jaw retaining assembly (610) together. For example, first and second metallic portions (612, 614) may be fixably coupled together using a variety of different methods, including using one or more coupling features and/or welding. As shown, two-piece distal MIM clip applier jaws are welded using welds (633) to stamped or laser cut proximal spring features to provide improved clip support and control. In this "split jaw" arrangement, each of first and second jaws (616a-b) is MIMed or stamped separately and then assembled or welded during the assembly process.

F. Sixth Exemplary Jaw Retaining Assembly

Figure 25:
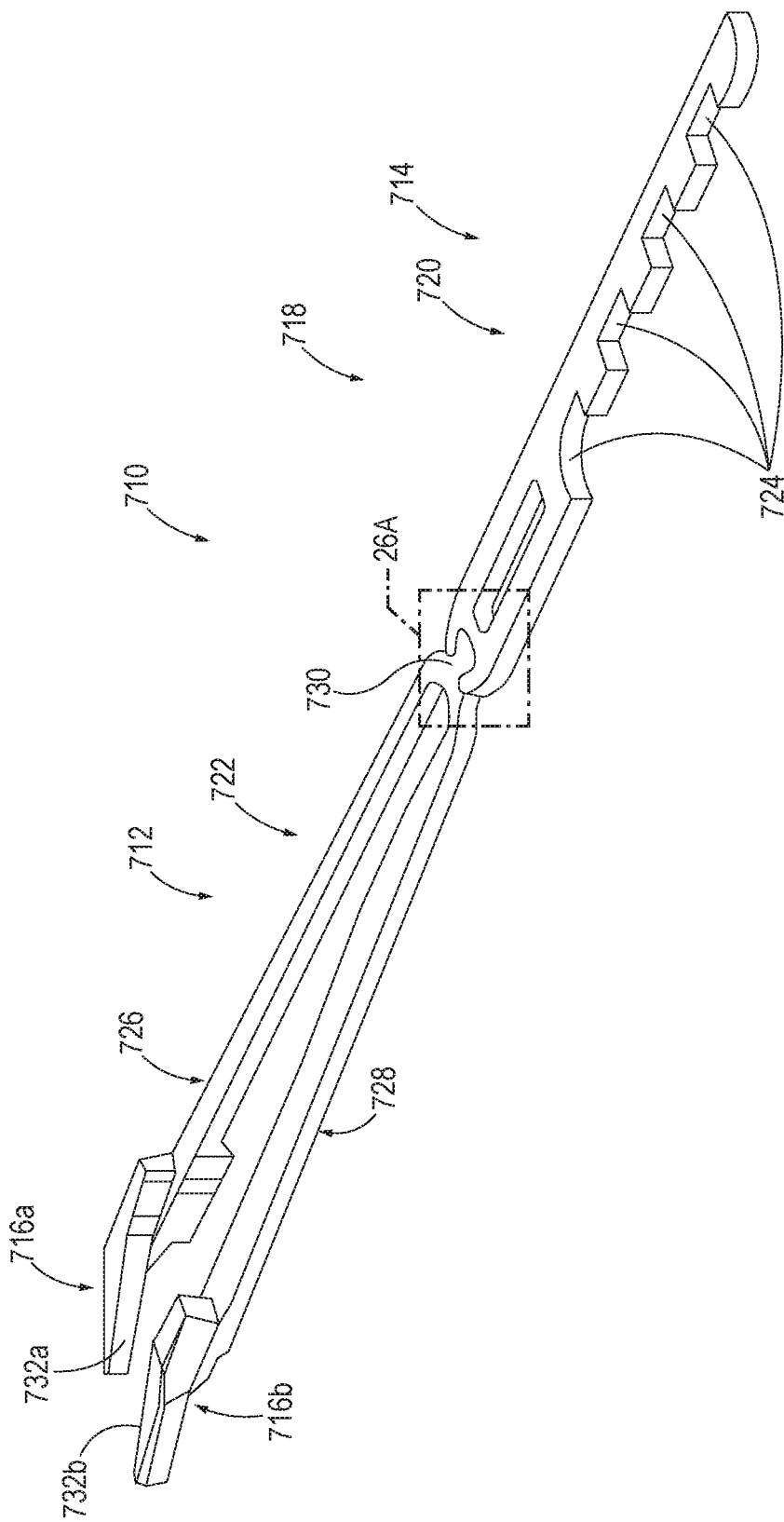
FIG. 25 depicts a front perspective view of a sixth exemplary jaw retaining assembly with proximal and distal portions coupled together.

FIGS. 25-26B show a sixth exemplary jaw retaining assembly (710) that includes first and second metallic portions (712, 714). Jaw retaining assembly (710) includes first and second opposing jaws (716a-b) extending distally from a shaft (718). As shown, shaft (718) includes a proximal portion (720) and a distal portion (722). FIG. 26A shows first and second metallic portions (712, 714) coupled together, while FIG. 26B shows a first and second metallic portions (712, 714) separated from each other. More specifically, FIG. 26A shows proximal and distal portions (720, 722) coupled together, while FIG. 26B shows proximal and distal portions (720, 722) separated from each other.

As shown, shaft (718) includes first and second arms (726, 728) extending distally from a fork point (730) of shaft (718). Fork point (730) separates first and second arms (726, 728). It is desirable that fork point (730) to be sufficiently flexible to allow for first and second jaws (716a-b) to move relative to one another. Conversely, at least first and second clip contact surfaces (732a-b) of first and second jaws (716a-b) are rigid and are intended to not significantly deform. This rigidity of first and second clip contact surfaces (732a-b) allows for improved clip control during clip advancement. Additionally, shaft (718) includes a plurality of apertures (724) having function to protrusions or teeth (94) shown and described with respect to FIG. 5. According to this exemplary embodiment, first metallic portion (712) includes first and second jaws (716a-b), first and second arms (726, 728), and proximal portion (720) of shaft (718). Second metallic portion (714) includes proximal portion (720) of shaft (718).

A method of manufacturing a surgical instrument, such as surgical clip applier (10), that is configured to apply a surgical clip to a patient is now described with respect FIGS. 26A-26B. The method includes metal injection molding first metallic portion (712) of jaw retaining assembly (710). As shown in FIGS. 26A-26B, first metallic portion (712) includes opposing first and second jaws (716a-b). It is desirable that at least first and second clip contact surfaces (732a-b) of first and second jaws (716a-b) be formed through a MIM process. With continued reference to FIG. 26A-26B, second metallic portion (714) of jaw retaining assembly (710) is metal injection molding, stamping and/or laser cutting. First metallic portion (712) may be integrally formed together as a unitary piece and/or second metallic portion (714) may be integrally formed together as a unitary piece. Second metallic portion (714) is separately formed from first metallic portion (712).

As shown, the method also includes fixably coupling first and second metallic portions (712, 714) of jaw retaining assembly (710) together. For example, first and second metallic portions (712, 714) may be fixably coupled together using a variety of different methods, including using one or more coupling features and/or welding using exemplary welds (733). As shown in FIGS. 26A-26B, proximal portion (720) of shaft (718) includes a coupling feature (734) adjacent a distal end (736). Distal portion (722) of shaft (718) includes a coupling feature (738) adjacent a proximal end (740). As shown, coupling feature (734) is a recess having retention features (742) to securably lock proximal and distal portions (720, 722) of shaft (718) together. Additionally, coupling feature (738) is shown as having a neck portion (744) having a smaller cross-sectional area than a head portion (746). As such, an outer perimeter (748) of neck and head portions (744, 746) mates with an inner perimeter (750) of coupling feature (734).

G. Seventh Exemplary Jaw Retaining Assembly

Figure 29:
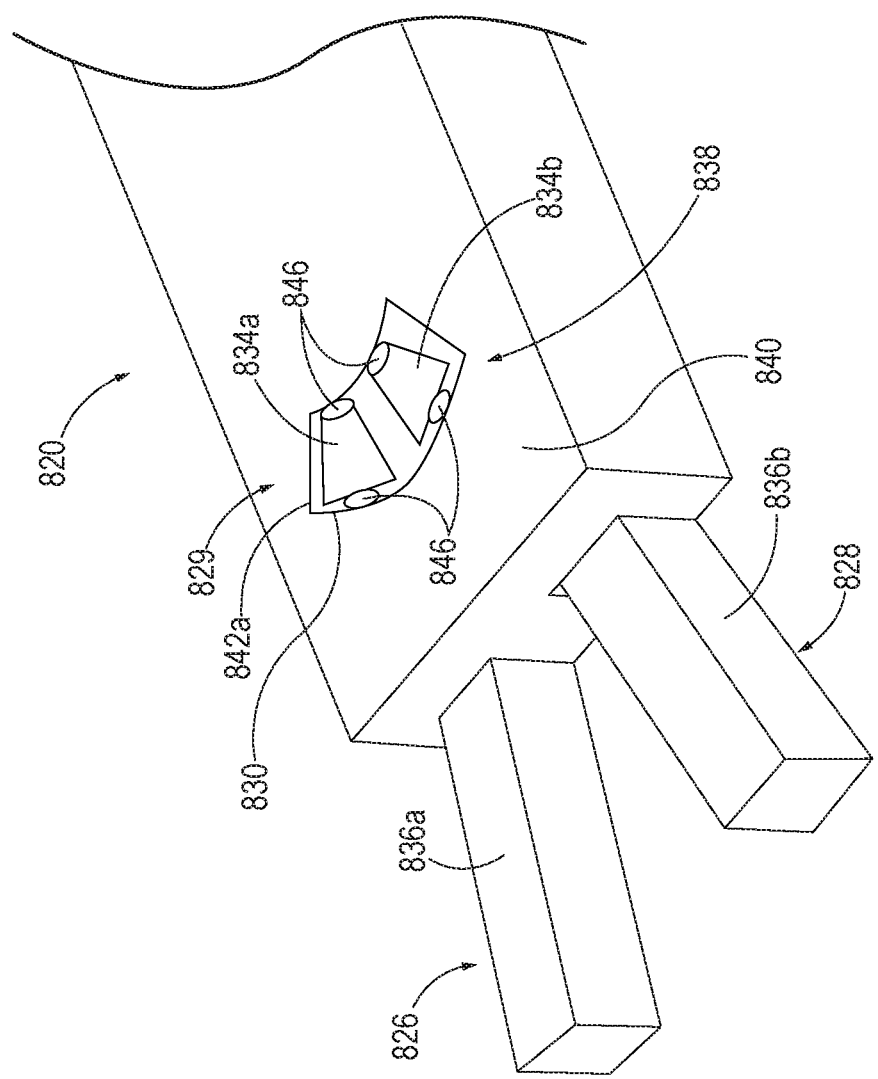
FIG. 29 depicts a bottom perspective view of the first and second jaws of FIG. 27 coupled with the shaft of FIG. 27.

FIGS. 27-29 show a seventh exemplary jaw retaining assembly (810) that includes first and second metallic portions (812, 814). Jaw retaining assembly (810) includes first and second opposing jaws (816a-b) extending distally from a shaft (818). As shown, shaft (818) includes a proximal portion (820) and a distal portion (822). FIG. 27 shows first and second metallic portions (812, 814) separated from each other, while FIG. 28 shows first and second metallic portions (812, 814) coupled together.

As shown, a first arm (826) extends proximally from first jaw (816a), and second arm (828) extends proximally from second jaw (816b). First and second arms (826, 828) fixably couple with proximal portion (820) of shaft (818) at a joint (829) as will be described with respect to FIGS. 28 and 29. First metallic portion (812) includes a fork point (830) which separates first and second arms (826, 828). It is desirable that fork point (830) be sufficiently flexible to allow for first and second jaws (816a-b) to move relative to one another. Conversely, it is desirable that first and second clip contact surfaces (832a-b) of first and second jaws (816a-b) be sufficiently rigid so as to not significantly deform. This rigidity of first and second clip contact surfaces (832a-b) allows for improved clip control during clip advancement. Additionally, shaft (818) includes a plurality of apertures (824) having function to protrusions or teeth (94) shown and described with respect to FIG. 5.

According to this exemplary embodiment, first metallic portion (812) includes first and second jaws (816a-b) and first and second arms (826, 828). As shown, first jaw (816a) and first arm (826) are integrally formed together as a unitary piece. Second jaw (816b) and second arm (828) are integrally formed together as a unitary piece. Second metallic portion (814) includes shaft (818) and is formed together as a unitary piece. Second metallic portion (814) is separately formed from first metallic portion (812).

A method of manufacturing a surgical instrument, such as surgical clip applier (10), that is configured to apply a surgical clip to a patient is now described with respect FIGS. 27-28. The method includes metal injection molding first metallic portion (812) of jaw retaining assembly (810). It is desirable that at least first and second clip contact surfaces (832a-b) of first and second jaws (816a-b) be formed through a MIM process. With continued reference to FIGS. 27-28, second metallic portion (814) of jaw retaining assembly (810) is formed by metal injection molding, stamping and/or laser cutting.

As shown, the method also includes fixably coupling first and second metallic portions (812, 814) of jaw retaining assembly (810) together. For example, first and second metallic portions (812, 814) may be fixably coupled together using a variety of different methods, including using one or more coupling features and/or welding. FIGS. 27 and 28 show first and second jaws (816a-b) that are completely separate prior to fixably coupling first and second metallic portions (812, 814) of jaw retaining assembly (810) together.

As shown in FIGS. 27-28, first metallic portion (812) includes a coupling features (834a-b) adjacent proximal ends (836a-b) of first and second arms (826, 828). As shown, coupling features (834a-b) include projections extending at right angles from the longitudinally extending first and second arms (826, 828). Second metallic portion (814) includes a coupling feature (838) adjacent a distal end (840). Coupling feature (838) is shown as first and second recesses (842a-b) that converge moving proximally. First and second recesses (842a-b) are separated at distal end (840) by a triangle shaped protrusion (844). Coupling features (834a-b, 838) securably lock proximal and distal portions (820, 822) of shaft (818) together.

As shown in FIGS. 28 and 29, bead welds (846) may be used to fixably secure first and second jaws (816a-b) coupled with shaft (818) in addition to or in lieu of coupling features (834a-b, 838). FIG. 29 shows a bottom perspective view of first and second jaws (816a-b) welded to shaft (818), where each of first and second arms (826, 828) is secured by two bead welds (846). However, it is envisioned that more or less discrete bead welds (846) may be used and/or may be substituted for a generally continuous weld.

H. Eighth Exemplary Jaw Retaining Assembly

Figure 30:
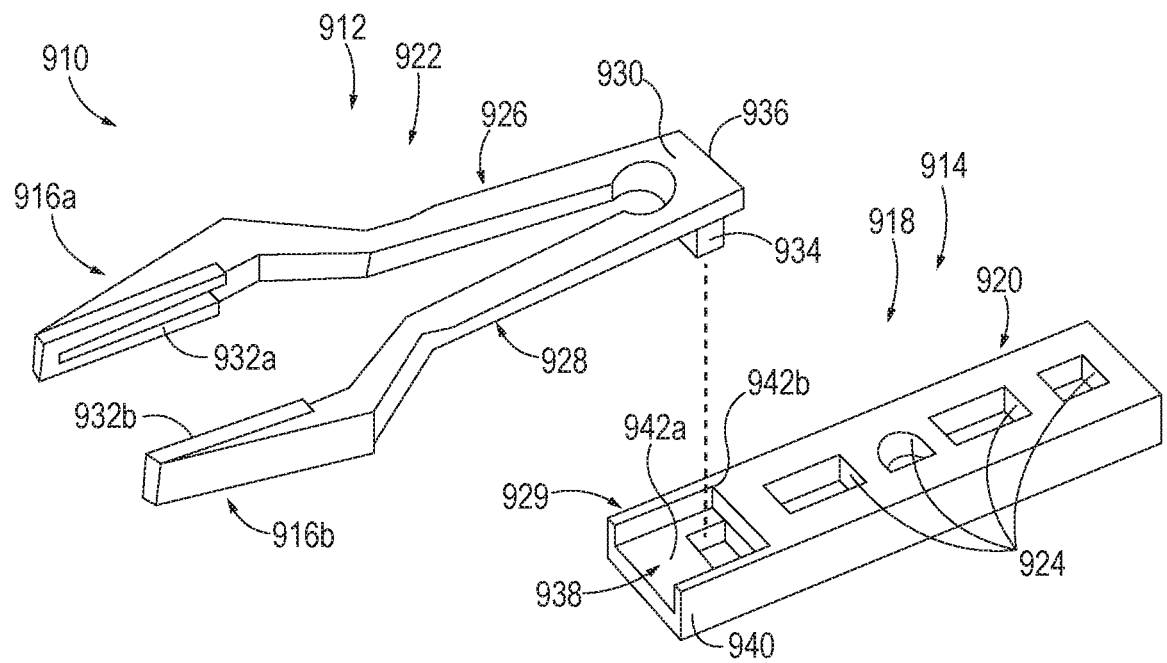
FIG. 30 depicts a front perspective view of an eighth exemplary jaw retaining assembly including first and second jaws integrally formed together and separate from a shaft.
Figure 31:
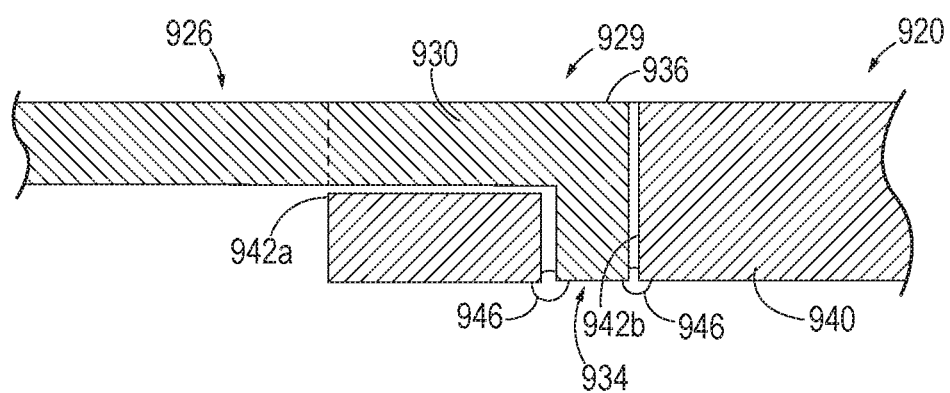
FIG. 31 depicts a sectional view of a portion of the jaw retaining assembly of FIG. 30 with the first jaw coupled with the shaft.

FIGS. 30-31 show an eighth exemplary jaw retaining assembly (910) that includes first and second metallic portions (912, 914). Jaw retaining assembly (910) includes first and second opposing jaws (916a-b) extending distally from a shaft (918). As shown, shaft (918) includes a proximal portion (920) and a distal portion (922). FIG. 30 shows first and second metallic portions (912, 914) separated from each other, while FIG. 31 shows first and second metallic portions (912, 914) coupled together.

As shown, a first arm (926) extends proximally from first jaw (916a), and second arm (928) extends proximally from second jaw (916b). First and second arms (926, 928) fixably couple with proximal portion (920) of shaft (918) at a joint (929). First metallic portion (912) includes a fork point (930) which separates first and second arms (926, 928). It is desirable that fork point (930) be sufficiently flexible to allow for first and second jaws (916a-b) to move relative to one another. Conversely, it is desirable that first and second clip contact surfaces (932a-b) of first and second jaws (916a-b) be sufficiently rigid so as to not significantly deform. This rigidity of first and second clip contact surfaces (932a-b) allows for improved clip control during clip advancement. Additionally, shaft (918) includes a plurality of apertures (924) having a similar function to protrusions or teeth (94) shown and described with respect to FIG. 5.

According to this exemplary embodiment, first metallic portion (912) includes first and second jaws (916a-b), first and second arms (926, 928), and fork point (830) which separates first and second arms (926, 928). As shown, first metallic portion (912), including first and second jaws (916a-b), first and second arms (926, 928), and fork point (930), are integrally formed together as a unitary piece. Second metallic portion (914) includes proximal portion (920) of shaft (918) may be formed together as a unitary piece. Second metallic portion (914) is separately formed from first metallic portion (912).

A method of manufacturing a surgical instrument, such as surgical clip applier (10), that is configured to apply a surgical clip to a patient is now described. The method includes metal injection molding first metallic portion (912) of jaw retaining assembly (910). It is desirable that at least first and second clip contact surfaces (932a-b) of first and second jaws (916a-b) be formed through a MIM process. With continued reference to FIGS. 30-31, second metallic portion (914) of jaw retaining assembly (910) is formed by metal injection molding, stamping and/or laser cutting.

As shown, the method also includes fixably coupling first and second metallic portions (912, 914) of jaw retaining assembly (910) together. For example, first and second metallic portions (912, 914) may be fixably coupled together using a variety of different methods, including using one or more coupling features and/or welding. FIGS. 30-31 show that first and second jaws (916a-b) are completely separate prior to fixably coupling first and second metallic portions (912, 914) of jaw retaining assembly (910) together.

As shown in FIGS. 30-31, first metallic portion (912) includes a coupling feature (934) adjacent proximal end (936) of first metallic portion (912). Coupling feature (934) is shown as a projection extending at a right angle from longitudinally extending first and second arms (926, 928). Second metallic portion (914) includes a coupling feature (938) adjacent a distal end (940) of second metallic portion (914). Coupling feature (938) is shown as first and second recesses (942a-b) having two different depths, where second recess (942b) extends deeper than first recess (942a). First and second recesses (942a-b) are shown as rectangular, however, a variety of shapes and sizes are also envisioned. Coupling features (934, 938) securably lock proximal and distal portions (920, 922) of shaft (918) together.

As shown in FIG. 31, bead welds (946) may be used to fixably secure first and second jaws (916a-b) coupled with shaft (918) in addition to or in lieu of coupling features (934, 938). However, it is envisioned that more or less discrete bead welds (946) may be used and/or may be substituted for a generally continuous weld.

III. EXEMPLARY CAMS

A. First Exemplary Cam

FIGS. 32-38 show a first exemplary cam (1010) that includes a first metallic portion (1012) and a second metallic portion (1014) that are fixably coupled together. A method of manufacturing a surgical instrument that includes opposing first and second jaws (96a-b, 216a-b, 316a-b, 416a-b, 516a-b, 616a-b, 716a-b, 816a-b, 916a-b) configured to apply a surgical clip to a patient is now described. Surgical instrument (10) may include cam (1010) configured to move opposing first and second jaws (216a-b, 316a-b, 416a-b, 516a-b, 616a-b, 716a-b, 816a-b, 916a-b) between open and closed positions, such as those shown in FIGS. 7A-7B.

The method includes metal injection molding at least first metallic portion (1012) of cam (1010). First metallic portion (1012) includes a tapering recess (1016) configured to slidably receive a portion of opposing first and second jaws (96a-b, 216a-b, 316a-b, 416a-b, 516a-b, 616a-b, 716a-b, 816a-b, 916a-b). The method also includes metal injection molding, stamping and/or laser cutting second metallic portion (1014) of cam (1010). First metallic portion (1012) may be completely separate from second metallic portion (1014). Proximal end (1018) of second metallic portion (1014) includes a keyed cutout (1020) having a similar structure and function to keyed cutout (100) of FIG. 6.

Figure 34:
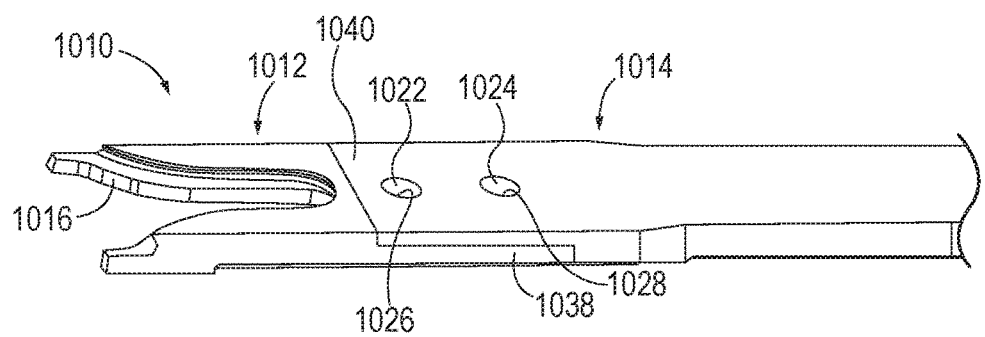
FIG. 34 depicts a cross-sectional perspective view of the cam of FIG. 33, taken along line 34-34 of FIG. 33.

The method also includes fixably coupling first and second metallic portions (1012, 1014) of cam (1010) together. FIG. 34 shows a cross-sectional perspective view of FIG. 33, taken along line 34-34 of FIG. 33 to better illustrate the coupling. As shown, first metallic portion (1012) includes proximal and distal pins (1022, 1024) configured to couple with proximal and distal recesses (1026, 1028) of second metallic portion (1014) to secure first and second metallic portions (1012, 1014) together. Additionally, second metallic portion (1014) includes first and second longitudinal projections (1030, 1032), configured to mate with first metallic portion (1012). Proximal and distal pins (1022, 1024) fixably couple a proximal end (1038) of first metallic portion (1012) with a distal end (1040) of second metallic portion (1014).

Figure 32:
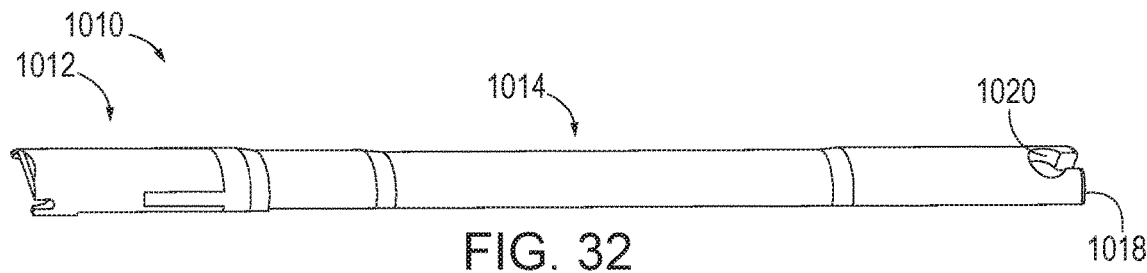
FIG. 32 depicts a front perspective view of a first exemplary cam including proximal and distal portions.
Figure 33:
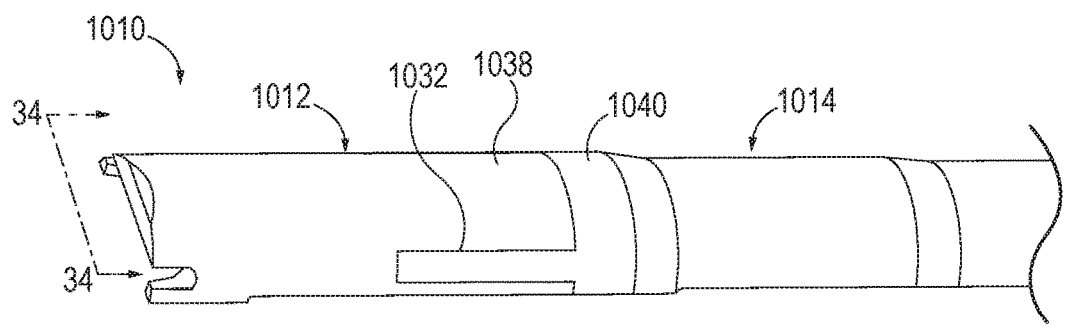
FIG. 33 depicts an enlarged front perspective view of the cam of FIG. 32.
Figure 35:
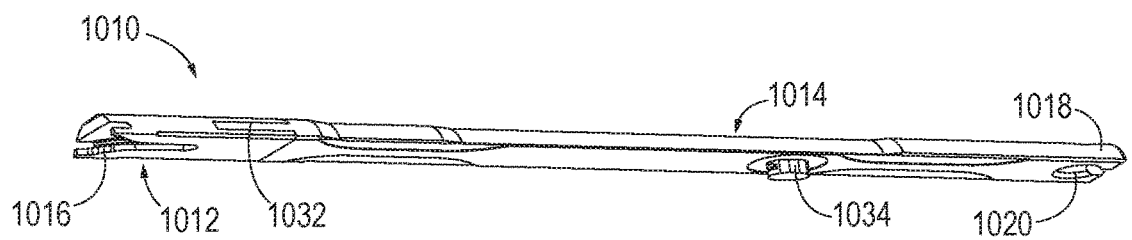
FIG. 35 depicts another perspective view of the cam of FIG. 32.
Figure 36:
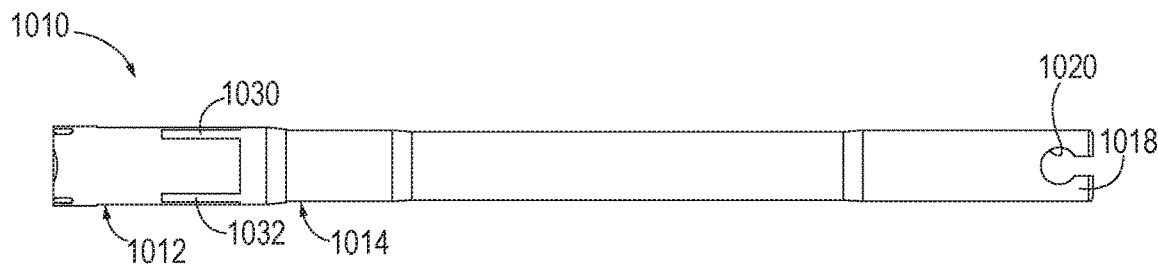
FIG. 36 depicts a top view of the cam of FIG. 32.
Figure 37:
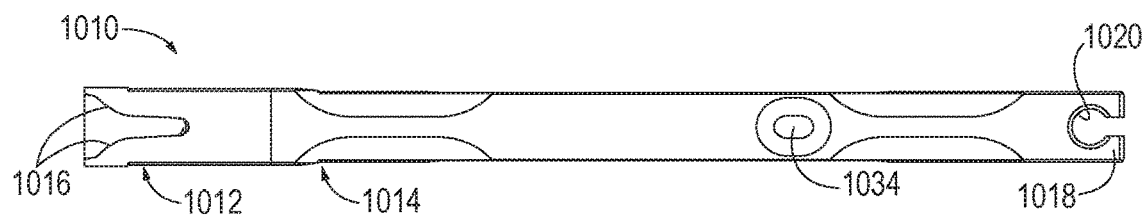
FIG. 37 depicts a bottom view of the cam of FIG. 32.
Figure 38:
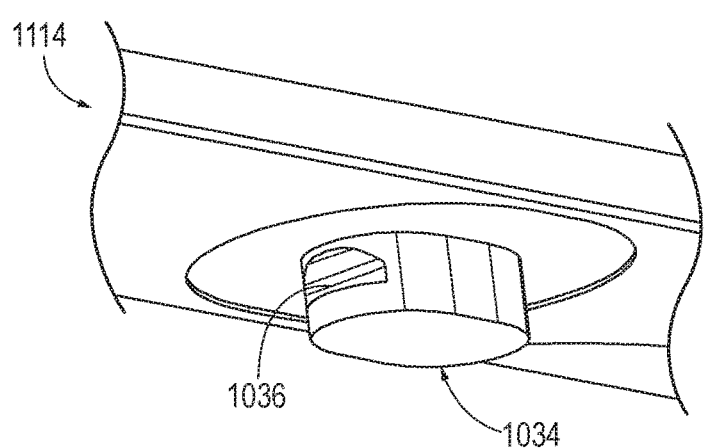
FIG. 38 depicts an enlarged perspective view of a portion of the cam of FIG. 35, showing a projection.

FIG. 36 shows a top view of cam of FIG. 32, while FIG. 37 shows a bottom view of cam of FIG. 32. Additionally, FIG. 38 shows an enlarged portion of cam of FIG. 35 showing a protrusion (1034) having a similar structure and function to protrusion (42c) of FIG. 6. Protrusion (1034) includes a cutout portion (1036).

B. Second Exemplary Cam

FIGS. 39-43 show a second exemplary cam (1110) that includes a first metallic portion (1112) and a second metallic portion (1114) that are fixably coupled together. A method of manufacturing a surgical instrument that includes opposing first and second jaws (96a-b, 216a-b, 316a-b, 416a-b, 516a-b, 616a-b, 716a-b, 816a-b, 916a-b) configured to apply a surgical clip to a patient is now described. Surgical instrument (10) includes cam (1110) configured to move opposing first and second jaws (216a-b, 316a-b, 416a-b, 516a-b, 616a-b, 716a-b, 816a-b, 916a-b) between open and closed positions.

The method includes metal injection molding at least first metallic portion (1112) of cam (1110). First metallic portion (1112) includes a tapering recess (1116) configured to slidably receive a portion of opposing first and second jaws (96a-b, 216a-b, 316a-b, 416a-b, 516a-b, 616a-b, 716a-b, 816a-b, 916a-b). The method also includes metal injection molding, stamping and/or laser cutting second metallic portion (1114) of cam (1110). First metallic portion (1112) may be completely separate from second metallic portion (1114). Proximal end (1118) of second metallic portion (1114) includes keyed cutout (1120).

Figure 41:
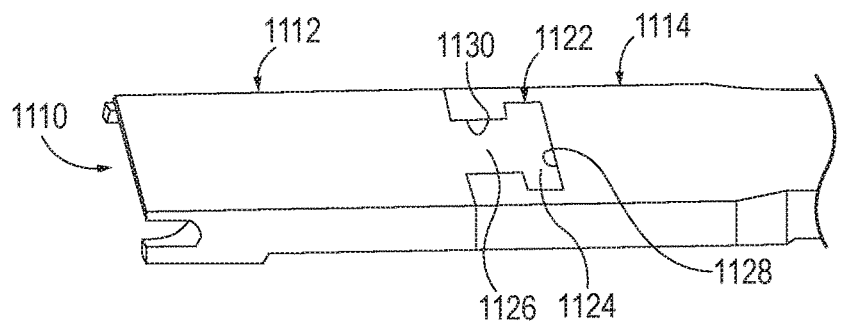
FIG. 41 depicts a cross-sectional perspective view of the cam of FIG. 40, taken along line 41-41 of FIG. 40.
Figure 42:
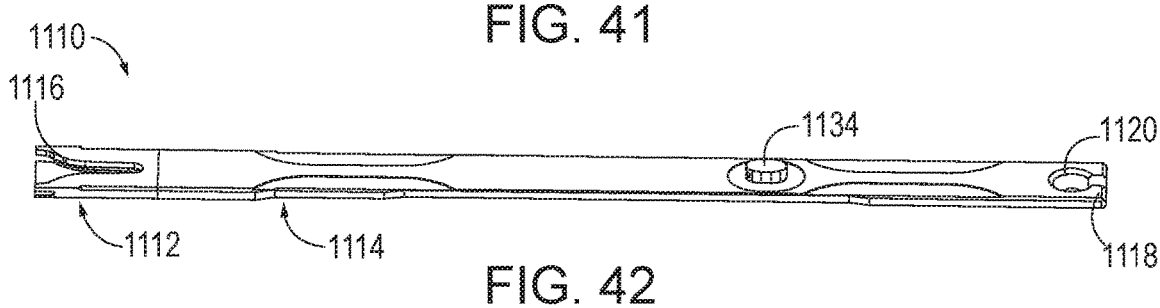
FIG. 42 depicts a bottom perspective view of the cam of FIG. 39.
Figure 43:
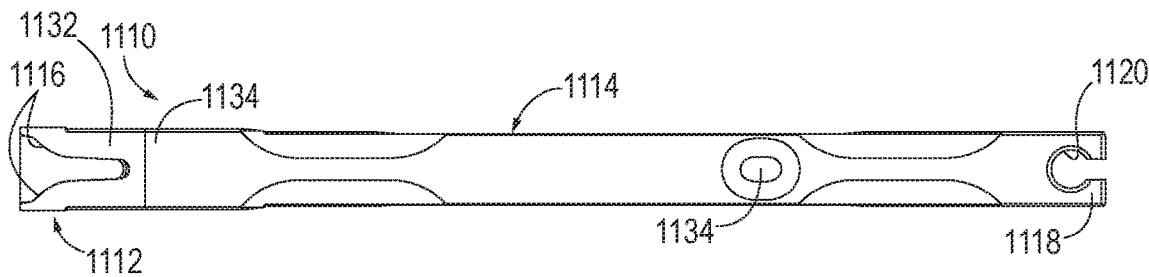
FIG. 43 depicts a bottom view of the cam of FIG. 39.

The method also includes fixably coupling first and second metallic portions (1112, 1114) of cam (1110) together. FIG. 41 shows a cross-sectional perspective view of FIG. 40, taken along line 41-41 of FIG. 40 to better illustrate the coupling. As shown, first metallic portion (1112) includes a bolt shaped projection (1122) having a head portion (1124) and a neck portion (1126). Head and neck portions (1124, 1126) are annular, but are shown in cross-section in FIG. 41. Bolt shaped projection (1122) is configured to fixably couple with first and second recessed portions (1128, 1130) of second metallic portion (1114) to secure first and second metallic portions (1112, 1114) together. Bolt shaped projection (1122) fixably couples a proximal end (1132) of first metallic portion (1112) with a distal end (1134) of second metallic portion (1114).

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of manufacturing a surgical instrument configured to apply a surgical clip to a patient, wherein the surgical instrument comprises a jaw retaining assembly, wherein the jaw retaining assembly includes a shaft and opposing first and second jaws, wherein the method comprises: (a) metal injection molding a first metallic portion of the jaw retaining assembly; (b) forming a second metallic portion of the jaw retaining assembly through one or more of metal injection molding, stamping, or laser cutting, wherein the second metallic portion is separately formed from the first metallic portion; and (c) fixably coupling the first and second metallic portions of the jaw retaining assembly together.

Example 2

The method of Example 1, wherein fixably coupling the first and second metallic portions comprises welding the first and second metallic portions of the jaw retaining assembly together.

Example 3

The method of any one or more of Examples 1 through 2, wherein the first metallic portion includes the first and second jaws, wherein the second metallic portion includes the shaft, wherein the shaft includes first and second arms extending distally from a fork point of the shaft, wherein the fork point separates the first and second arms, wherein fixably coupling the first and second metallic portions of the jaw retaining assembly together further comprises: (i) fixably coupling the first jaw with the first arm at a first joint, and (ii) fixably coupling the second jaw with the second arm at a second joint.

Example 4

The method of Example 3, wherein fixably coupling the first arm with the first jaw at the first joint further comprises fixably coupling a first pin of the first arm or the first jaw with a corresponding recess formed in the other of the first arm or the first jaw, wherein fixably coupling the second arm with the second jaw at the second joint further comprises fixably coupling a second pin of the second arm or the second jaw with a corresponding recess formed in the other of the second arm or the second jaw.

Example 5

The method of Example 3, wherein fixably coupling the first arm with the first jaw at the first joint further comprises fixably coupling first and second pins of the first arm or the first jaw with first and second corresponding recesses formed in the other of the first arm or the first jaw, wherein fixably coupling the second arm with the second jaw at the second joint further comprises fixably coupling third and fourth pins of the second arm or the second jaw with third and fourth corresponding recesses formed in the other of the second arm or the second jaw.

Example 6

The method of any one or more of Examples 3 through 5, wherein the first joint is adjacent a proximal end of the first jaw and a distal end of the first arm, wherein the second joint is adjacent a proximal end of the second jaw and a distal end of the second arm.

Example 7

The method of any one or more of Examples 3 through 6, wherein the first joint is disposed proximal to a first clip contact surface of the first jaw and distal to the fork point that separates the first and second arms, wherein the first clip contact surface is configured to contact the surgical clip, wherein the second joint is disposed proximal to a second clip contact surface of the second jaw and distal to the fork point that separates the first and second arms, wherein the second clip contact surface is configured to contact the surgical clip.

Example 8

The method of any one or more of Examples 1 through 2, wherein the first metallic portion includes the first and second jaws that extend distally from respective first and second arms, wherein the first and second arms are joined at a fork point that is integrally formed as a unitary piece together with the first and second arms and the first and second jaws, wherein a proximal end of the first metallic portion includes a first coupling feature, and wherein the shaft includes a second coupling feature, wherein fixably coupling the first and second metallic portions together further comprises fixably coupling the first coupling feature of the proximal end with the second coupling feature of the shaft.

Example 9

The method of any one or more of Examples 1 through 2, wherein the first metallic portion includes the first and second jaws that extend distally from respective first and second arms, wherein the first arm includes a first arm coupling feature and the second arm includes a second arm coupling feature, wherein the second metallic portion includes the shaft, wherein the shaft includes first and second shaft coupling features, wherein fixably coupling the first and second metallic portions further comprises: (i) fixably coupling the first arm coupling feature of the first jaw with the first shaft coupling feature, and (ii) fixably coupling the second arm coupling feature of the second jaw with the second shaft coupling feature.

Example 10

The method of Example 9, wherein the first shaft coupling feature or the first arm coupling feature includes an arcuate hook, wherein the other the first shaft coupling feature or the first arm coupling feature includes correspondingly shaped receptacle, wherein the method further comprises rotating the arcuate hook into alignment with the correspondingly shaped receptacle prior to fixably coupling the arcuate hook with the correspondingly shaped receptacle.

Example 11

The method of Example 10, wherein fixably coupling the arcuate hook with the correspondingly shaped receptacle further comprises welding the arcuate hook with the correspondingly shaped receptacle to secure the first and second metallic portions together.

Example 12

The method of Example 1, wherein the first metallic portion includes first and second distal shoes, wherein the second metallic portion includes first and second interior portions of the first and second jaws, wherein fixably coupling the first and second metallic portions further comprises: (i) fixably coupling interior surfaces of the first distal shoe with exterior surfaces of the first interior portion, and (ii) fixably coupling interior surfaces of the second distal shoe with exterior surfaces of the second interior portion.

Example 13

The method of Example 12, wherein prior to fixably coupling the first distal shoe with the first arm and fixably coupling the second distal shoe with the second arm, the method further comprises: (a) aligning the first distal shoe to at least partially surround at least three walls of the first jaw; and (b) aligning the second distal shoe to at least partially surround at least three walls of the second jaw.

Example 14

The method of any one or more of Examples 1 through 2, wherein the shaft includes proximal and distal portions, wherein the distal portion includes first and second arms, wherein the first metallic portion includes the first jaw, the first arm and a portion of the proximal portion, wherein the second metallic portion includes the second jaw, the second arm, and a portion of the proximal portion.

Example 15

The method of any one or more of Examples 1 through 2, wherein the first and second jaws that extend distally from respective first and second arms, wherein the first and second arms are completely separate prior to fixably coupling the first and second metallic portions of the jaw retaining assembly together.

Example 16

The method of any one or more of Examples 1 through 2, wherein the first and second jaws that extend distally from respective first and second arms, wherein the first and second arms are fixably coupled to each other at a coupling point prior to fixably coupling the first and second metallic portions of the jaw retaining assembly together.

Example 17

A method of manufacturing a surgical instrument configured to apply a surgical clip to a patient, wherein the surgical instrument comprises a jaw retaining assembly, wherein the jaw retaining assembly includes a shaft and opposing first and second jaws, wherein the method comprises: (a) metal injection molding a first metallic portion of the jaw retaining assembly, wherein the first metallic portion includes first and second jaw clip guidance features of the first and second jaws; (b) metal injection molding a second metallic portion of the jaw retaining assembly, wherein the second metallic portion is completely separate from the first metallic portion, wherein the second metallic portion includes a bearing jaw portion; and (c) welding the first and second metallic portions of the jaw retaining assembly together.

Example 18

The method of Example 17, wherein the first metallic portion includes the first and second jaws, wherein the second metallic portion includes the shaft, wherein the shaft includes first and second arms extending distally from a fork point of the bearing jaw portion of the shaft, wherein the fork point separates the first and second arms, wherein the method further comprises: (a) welding first pin of the first arm or the first jaw with a corresponding recess formed in the other of the first arm or the first jaw at a first joint; and (b) welding a second pin of the second arm or the second jaw with a corresponding recess formed in the other of the second arm or the second jaw at a second joint.

Example 19

A method of manufacturing a surgical instrument that includes a pair of opposing jaws configured to apply a surgical clip to a patient, wherein the surgical instrument comprises a cam configured to move the opposing jaws between open and closed position, wherein the cam includes proximal and distal metallic portions, wherein the method comprises: (a) metal injection molding the distal metallic portion of the cam, wherein the distal metallic portion includes a tapering recess configured to slidably receive a portion of the opposing jaws; (b) forming the proximal metallic portion of the cam through one or more of metal injection molding, stamping, or laser cutting; and (c) fixably coupling the proximal and distal metallic portions of the cam together.

Example 20

The method of Example 19, wherein the distal metallic portion of the cam includes a distal coupling feature and the proximal metallic portion of the cam includes a proximal coupling feature, wherein fixably coupling the distal and proximal metallic portions together further comprises fixably coupling the distal coupling feature of the distal metallic portion with the proximal coupling feature of the proximal metallic portion.

Example 21

A surgical instrument configured to apply a surgical clip to a patient, wherein the surgical instrument comprises: a jaw retaining assembly that includes first and second metallic portions, wherein the first metallic portion includes at least a portion of at least one of a shaft, a first jaw, or a second jaw, wherein the first metallic portion is formed by metal injection molding, wherein the second portion includes at least a separate portion of at least one of a shaft, a first jaw, or a second jaw, wherein the second metallic portion is formed through one or more of metal injection molding, stamping, or laser cutting, wherein the second metallic portion is separately formed from the first metallic portion, and wherein the first and second metallic portions of the jaw retaining assembly are fixably coupled together.

Example 22

The instrument of Example 21, wherein the first and second metallic portions of the jaw retaining assembly are welded together.

Example 23

The instrument of any one or more of Examples 21 through 22, wherein the first metallic portion includes the first and second jaws, wherein the second metallic portion includes the shaft, wherein the shaft includes first and second arms extending distally from a fork point of the shaft, wherein the fork point separates the first and second arms, wherein the first jaw is fixably coupled with the first arm at a first joint and the second jaw is fixably coupled with the second arm at a second joint.

Example 24

The instrument of any one or more of Examples 21 through 23, wherein a first pin of the first arm or the first jaw is fixably coupled with a corresponding recess formed in the other of the first arm or the first jaw, wherein a second pin of the second arm or the second jaw is fixably coupled with a corresponding recess formed in the other of the second arm or the second jaw.

Example 25

The instrument of any one or more of Examples 21 through 23, wherein first and second pins of the first arm or the first jaw are fixably coupled with first and second corresponding recesses formed in the other of the first arm or the first jaw, wherein third and fourth pins of the second arm or the second jaw are fixably coupled with third and fourth corresponding recesses formed in the other of the second arm or the second jaw.

Example 26

The instrument of Example 23, wherein the first joint is adjacent a proximal end of the first jaw and a distal end of the first arm, wherein the second joint is adjacent a proximal end of the second jaw and a distal end of the second arm.

Example 27

The instrument of Example 23, wherein the first joint is disposed proximal to a first clip contact surface of the first jaw and distal to the fork point that separates the first and second arms, wherein the first clip contact surface is configured to contact the surgical clip, wherein the second joint is disposed proximal to a second clip contact surface of the second jaw and distal to the fork point that separates the first and second arms, wherein the second clip contact surface is configured to contact the surgical clip.

Example 28

The instrument of any one or more of Examples 21 through 22, wherein the first metallic portion includes the first and second jaws that extend distally from respective first and second arms, wherein the first and second arms are joined at a fork point that is integrally formed as a unitary piece together with the first and second arms and the first and second jaws, wherein a proximal end of the first metallic portion includes a first coupling feature, wherein the shaft includes a second coupling feature, wherein the first coupling feature of the proximal end is fixably coupled with the second coupling feature of the shaft.

Example 29

The instrument of any one or more of Examples 21 through 22, wherein the first metallic portion includes the first and second jaws that extend distally from respective first and second arms, wherein the first arm includes a first arm coupling feature and the second arm includes a second arm coupling feature, wherein the second metallic portion includes the shaft, wherein the shaft includes first and second shaft coupling features, wherein the first arm coupling feature of the first jaw is fixably coupled with the first shaft coupling feature and the second arm coupling feature of the second jaw is fixably coupled with the second shaft coupling feature.

Example 30

The instrument of any one or more of Examples 21 through 22, wherein the first shaft coupling feature or the first arm coupling feature includes an arcuate hook, wherein the other the first shaft coupling feature or the first arm coupling feature includes correspondingly shaped receptacle, wherein the arcuate hook is rotated into alignment with the correspondingly shaped receptacle prior to fixably coupling the arcuate hook with the correspondingly shaped receptacle.

Example 31

The instrument of Example 30, wherein the arcuate hook is welded with the correspondingly shaped receptacle to secure the first and second metallic portions together.

Example 32

The instrument of Example 21, wherein the first metallic portion includes first and second distal shoes, wherein the second metallic portion includes first and second interior portions of the first and second jaws, wherein interior surfaces of the first distal shoe are fixably coupled with exterior surfaces of the first interior portion, and interior surfaces of the second distal shoe are fixably coupled with exterior surfaces of the second interior portion.

Example 33

The instrument of Example 32, wherein prior to fixably coupling the first distal shoe with the first arm and fixably coupling the second distal shoe with the second arm, the first distal shoe is aligned to at least partially surround at least three walls of the first jaw and the second distal shoe is aligned to at least partially surround at least three walls of the second jaw.

Example 34

The instrument of any one or more of Examples 21 through 22, wherein the shaft includes proximal and distal portions, wherein the distal portion includes first and second arms, wherein the first metallic portion includes the first jaw, the first arm and a portion of the proximal portion, wherein the second metallic portion includes the second jaw, the second arm, and a portion of the proximal portion.

Example 35

The instrument of any one or more of Examples 21 through 22, wherein the first and second jaws that extend distally from respective first and second arms, wherein the first and second arms are completely separate prior to fixably coupling the first and second metallic portions of the jaw retaining assembly together.

Example 36

The instrument of any one or more of Examples 21 through 22, wherein the first and second jaws extend distally from respective first and second arms, wherein the first and second arms are fixably coupled to each other at a coupling point prior to fixably coupling the first and second metallic portions of the jaw retaining assembly together.

Example 37

A surgical instrument configured to apply a surgical clip to a patient, wherein the surgical instrument comprises: a jaw retaining assembly that includes first and second metallic portions, wherein the first metallic portion includes at least a portion of at least one of a shaft, a first jaw, or a second jaw, wherein the first metallic portion is formed by metal injection molding, wherein the second portion includes at least a separate portion of at least one of a shaft, a first jaw, or a second jaw, wherein the second metallic portion is formed by metal injection molding, wherein the second metallic portion is completely separate from the first metallic portion, wherein the second metallic portion includes a bearing jaw portion, wherein the first and second metallic portions of the jaw retaining assembly are welded together.

Example 38

The instrument of Example 37, wherein the first metallic portion includes the first and second jaws, wherein the second metallic portion includes the shaft, wherein the shaft includes first and second arms extending distally from a fork point of the shaft, wherein the fork point separates the first and second arms, wherein the first pin of the first arm or the first jaw is welded with a corresponding recess formed in the other of the first arm or the first jaw at a first joint, wherein a second pin of the second arm or the second jaw is welded with a corresponding recess formed in the other of the second arm or the second jaw at a second joint.

Example 39

A surgical instrument configured to apply a surgical clip to a patient, wherein the surgical instrument comprises: a pair of opposing jaws configured to apply a surgical clip to a patient; and a cam configured to move the opposing jaws between open and closed position, wherein the cam includes proximal and distal metallic portions, wherein the proximal metallic portion of the cam is formed through one or more of metal injection molding, stamping, or laser cutting, wherein the distal metallic portion of the cam is formed through metal injection molding, wherein the distal metallic portion includes a tapering recess configured to slidably receive a portion of the opposing jaws, wherein the proximal and distal metallic portions of the cam are fixably coupled together.

Example 40

The instrument of Example 39, wherein the distal metallic portion of the cam includes a distal coupling feature and the proximal metallic portion of the cam includes a proximal coupling feature, wherein the distal coupling feature of the distal metallic portion is fixably coupled with the proximal coupling feature of the proximal metallic portion.

Example 41

A surgical instrument comprising: (a) a housing; (b) an elongate shaft extending distally from the housing; and (c) a jaw retaining assembly coupled with the elongate shaft, wherein the jaw retaining assembly includes: (i) a first metallic portion that includes a least a portion of opposing first and second jaws, and (ii) a second metallic portion that includes at least a portion of a shaft, wherein the first metallic portion of the jaw retaining assembly is formed using metal injection molding, and wherein the second metallic portion of the jaw retaining assembly is formed by one or more of metal injection molding, stamping, or laser cutting, wherein the second metallic portion is separately formed from the first metallic portion; wherein the first and second metallic portions are fixably coupled together.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a surgical instrument configured to apply a surgical clip to a patient, wherein the surgical instrument comprises a jaw retaining assembly, wherein the jaw retaining assembly includes a shaft and opposing first and second jaws, wherein the method comprises:
   (a) metal injection molding the first and second jaws of a first metallic portion of the jaw retaining assembly;
   (b) forming first and second arms of a second metallic portion of the jaw retaining assembly through one or more of metal injection molding, stamping, or laser cutting, wherein the second metallic portion is separately formed from the first metallic portion; and
   (c) fixably coupling the first and second metallic portions of the jaw retaining assembly together by coupling at least one of a first coupling feature or a first recess disposed at a proximal end of the first jaw with at least one of the other of the first coupling feature or the first recess disposed at a distal end of the first arm.

2. The method of claim 1, wherein fixably coupling the first and second metallic portions comprises welding the first and second metallic portions of the jaw retaining assembly together.

3. The method of claim 1, wherein the first and second jaws extend distally from the respective first and second arms, wherein the first and second arms are completely separate prior to fixably coupling the first and second metallic portions of the jaw retaining assembly together.

4. The method of claim 1, wherein coupling the first coupling feature with the first recess further comprises welding using at least one weld the first coupling feature with the first recess.

5. The method of claim 1, wherein the second metallic portion includes the shaft, wherein the first and second arms extend distally from a fork point of the shaft, wherein the fork point separates the first and second arms, wherein fixably coupling the first and second metallic portions of the jaw retaining assembly together further comprises:
   (i) fixably coupling the first jaw with the first arm at a first lap joint, and
   (ii) fixably coupling the second jaw with the second arm at a second lap joint.

6. The method of claim 5, wherein the first lap joint is adjacent the proximal end of the first jaw and the distal end of the first arm, wherein the second lap joint is adjacent the proximal end of the second jaw and the distal end of the second arm.

7. The method of claim 5, wherein the first lap joint is disposed proximal to a first clip contact surface of the first jaw and distal to the fork point that separates the first and second arms, wherein the first clip contact surface is configured to contact the surgical clip, wherein the second lap joint is disposed proximal to a second clip contact surface of the second jaw and distal to the fork point that separates the first and second arms, wherein the second clip contact surface is configured to contact the surgical clip.

8. The method of claim 1, wherein fixably coupling further comprises coupling at least one of a second coupling feature or a second recess disposed at a proximal end of the second jaw with at least one of the other of the second coupling feature or the second recess disposed at a distal end of the second arm.

9. The method of claim 8, wherein coupling the second coupling feature with the second recess further comprises welding using at least one weld the second coupling feature with the second recess.

10. The method of claim 8, wherein the first coupling feature includes a first pin disposed at the proximal end of the first jaw, wherein the second coupling feature includes a second pin disposed at the proximal end of the second jaw.

11. The method of claim 10, wherein the first pin is a cylindrical projection extending from an interior surface of the first jaw, wherein the second pin is a cylindrical projection extending from an interior surface of the second jaw.

12. The method of claim 11, wherein the first coupling feature includes a third pin disposed at the proximal end of the first jaw, wherein the second coupling feature includes a fourth pin disposed at the proximal end of the second jaw.

13. A method of manufacturing a surgical instrument configured to apply a surgical clip to a patient, wherein the surgical instrument comprises a jaw retaining assembly, wherein the jaw retaining assembly includes a shaft and opposing first and second jaws, wherein the method comprises:
   (a) metal injection molding the first and second jaws of a first metallic portion of the jaw retaining assembly, wherein the first metallic portion includes first and second jaw clip guidance features of the first and second jaws;
   (b) metal injection molding first and second arms of a second metallic portion of the jaw retaining assembly, wherein the second metallic portion is completely separate from the first metallic portion, wherein the first arm includes wherein the second metallic portion includes a bearing jaw portion;
   (c) aligning a proximal lap surface of the first jaw with a distal lap surface of the first arm;
   (d) aligning a proximal lap surface of the second jaw with a distal lap surface of the second arm; and
   (e) welding the first and second metallic portions of the jaw retaining assembly together.

14. The method of claim 13, wherein the second metallic portion includes the shaft, wherein the shaft includes first and second arms extending distally from a fork point of the bearing jaw portion of the shaft, wherein the fork point separates the first and second arms, wherein the method further comprises:
   (a) welding a first pin of the first arm or the first jaw with a corresponding recess formed in the other of the first arm or the first jaw at a first joint; and
   (b) welding a second pin of the second arm or the second jaw with a corresponding recess formed in the other of the second arm or the second jaw at a second joint.

15. The method of claim 13, further comprising aligning a proximal lap surface of the second jaw with a distal lap surface of the second arm.

16. A method of manufacturing a surgical instrument configured to apply a surgical clip to a patient, wherein the surgical instrument comprises a jaw retaining assembly, wherein the jaw retaining assembly includes a shaft and opposing first and second jaws, wherein the method comprises:

(a) metal injection molding the first and second jaws of a first metallic portion of the jaw retaining assembly;
(b) forming first and second arms of a shaft of a second metallic portion of the jaw retaining assembly through one or more of metal injection molding, stamping, or laser cutting, wherein the second metallic portion is separately formed from the first metallic portion; and
(c) fixably coupling the first and second metallic portions of the jaw retaining assembly together by:
   (i) coupling a first coupling feature disposed at a proximal end of the first jaw with a first recess disposed at a distal end of the first arm, and
   (ii) coupling a second coupling feature disposed at a proximal end of the second jaw with a second recess disposed at a distal end of the second arm.

17. The method of claim 16, wherein the first coupling feature includes a first pin disposed at the proximal end of the first jaw, wherein the second coupling feature includes a second pin disposed at the proximal end of the second jaw.

18. The method of claim 17, wherein the first coupling feature includes a third pin disposed at the proximal end of the first jaw, wherein the second coupling feature includes a fourth pin disposed at the proximal end of the second jaw.

* * * * *